United States Patent
Leuwer et al.

(10) Patent No.: US 10,442,814 B2
(45) Date of Patent: Oct. 15, 2019

(54) PHARMACOLOGICALLY ACTIVE COMPOUNDS

(71) Applicant: The University of Liverpool, Liverpool (GB)

(72) Inventors: Martin Leuwer, Liverpool (GB); Paul M. O'Neill, Liverpool (GB); Neil Berry, Liverpool (GB); Chandrakala Pidathala, Liverpool (GB)

(73) Assignee: University of Liverpool, Liverpool (GB)

( * ) Notice: Subject to any disclaimer, the term of this patent is extended or adjusted under 35 U.S.C. 154(b) by 0 days.

(21) Appl. No.: 15/953,109

(22) Filed: Apr. 13, 2018

(65) Prior Publication Data

US 2019/0084993 A1    Mar. 21, 2019

Related U.S. Application Data

(63) Continuation of application No. 15/587,068, filed on May 4, 2017, now Pat. No. 9,944,653, which is a
(Continued)

(30) Foreign Application Priority Data

Dec. 23, 2013 (GB) .................... 1322905.9

(51) Int. Cl.
*C07D 491/107* (2006.01)
*C07D 205/04* (2006.01)
(Continued)

(52) U.S. Cl.
CPC .......... *C07D 491/107* (2013.01); *A61P 23/00* (2018.01); *A61P 25/00* (2018.01);
(Continued)

(58) Field of Classification Search
None
See application file for complete search history.

(56) References Cited

U.S. PATENT DOCUMENTS 9,676,786 B2   6/2017   Leuwer et al.
9,944,653 B2   4/2018   Li et al.
(Continued)

FOREIGN PATENT DOCUMENTS

WO   WO-2005/063665 A1   7/2005
WO   WO-2005/077896 A1   8/2005

OTHER PUBLICATIONS

"Crystilization and Precipitation," in Ullmann's Encyclopedia of Industrial Chemistry, Copyright 2002 by Wiley-VCH Verlag GmbH & Co. KGaA, pp. 1-51.
(Continued)

*Primary Examiner* — Karl J Puttlitz
(74) *Attorney, Agent, or Firm* — Foley Hoag LLP; David P. Halstead; Lucas P. Watkins

(57) ABSTRACT

The present invention relates to compounds of formula I shown below:

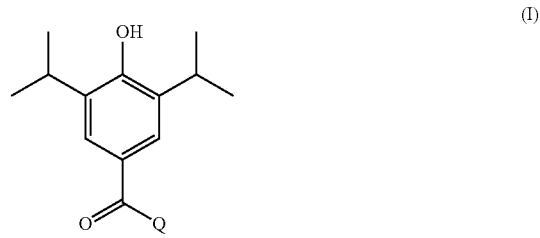

wherein Q is as defined herein. The compounds of formula I act as selective positive allosteric modulators of strych-
(Continued)

nine-sensitive alpha 1-glycine receptors. The present invention further relates to the use of these compounds as therapeutic agents for the treatment and/or prevention of diseases or conditions in which strychnine-sensitive alpha 1-glycine receptor activity is implicated (such as, for example, chronic pain. The present invention also relates to processes for the preparation of these compounds and to pharmaceutical compositions comprising them.

15 Claims, 10 Drawing Sheets

Related U.S. Application Data continuation of application No. 15/107,653, filed as application No. PCT/GB2014/053838 on Dec. 23, 2014, now Pat. No. 9,676,786.

(51) Int. Cl.
| | | |
|---|---|---|
| C07D 265/30 | (2006.01) | |
| C07D 493/10 | (2006.01) | |
| C07D 295/192 | (2006.01) | |
| C07D 211/06 | (2006.01) | |
| A61P 25/00 | (2006.01) | |
| A61P 23/00 | (2006.01) | |

(52) U.S. Cl.
CPC .......... *C07D 205/04* (2013.01); *C07D 211/06* (2013.01); *C07D 265/30* (2013.01); *C07D 295/192* (2013.01); *C07D 493/10* (2013.01)

(56) References Cited

U.S. PATENT DOCUMENTS

| | | | |
|---|---|---|---|
| 2005/0182041 A1* | 8/2005 | Altisen | C07D 205/04 |
| | | | 514/210.01 |
| 2007/0093469 A1* | 4/2007 | Cuberes Altisen | C07D 205/04 |
| | | | 514/210.17 |
| 2007/0142477 A1 | 6/2007 | Leuwer et al. | |
| 2012/0029235 A1 | 2/2012 | Leuwer et al. | |

OTHER PUBLICATIONS

International Search Report and Written Opinion for PCT/GB2014/05383 dated Mar. 4, 2015.
Kirk-Othmer Encyclopedia of Chemical Technology Coopyright 2002 by John Wiley & Sons, Inc., pp. 95-147, Article Online Posting Date: Aug. 16, 2002.
Rouhi, "The right stuff, from research and development to the clinic, getting drug crystals right is full of pitfalls," Chemical and Engineering News, 32-35 (2003).
UK Search Report for Application No. GB1322905.9 dated Jul. 15, 2014.

* cited by examiner

PHARMACOLOGICALLY ACTIVE COMPOUNDS

REFERENCE TO RELATED APPLICATIONS

This application is a continuation of U.S. application Ser. No. 15/587,068, filed May 4, 2017, which is a continuation of U.S. application Ser. No. 15/107,653, filed Jun. 23, 2016, which is the U.S. National Stage of International Patent Application No. PCT/GB2014/053838, filed Dec. 23, 2014, which claims the benefit of and priority to Great Britain Patent Application No. 1322905.9, filed Dec. 23, 2013. Each of the U.S. and International patent applications are hereby fully incorporated by reference herein.

INTRODUCTION

The present invention relates to pharmacologically active compounds. More specifically, the present invention relates to compounds that act as selective positive allosteric modulators of strychnine-sensitive alpha 1-glycine receptors. The present invention further relates to the use of these compounds as therapeutic agents for the treatment and/or prevention of diseases or conditions in which strychnine-sensitive alpha 1-glycine receptor activity is implicated (such as, for example, chronic pain or neuropathic pain). The present invention also relates to processes for the preparation of these compounds and to pharmaceutical compositions comprising them.

BACKGROUND OF THE INVENTION

In many clinical settings there is a need for safe and effective pain control strategies. However the majority of developments in the pain control field have failed to deliver high efficacy products free of undesirable side effects and safety issues. The opiates are generally regarded as the most effective treatment available for severe pain, but the ultimate goal is to deliver a pain control agent with the efficacy of the opiates but without the sedation, dependence, gastric damage and general tolerability problems that are associated with opiate use.

It has been postulated that phenol derivatives may have a number of neuromodulatory effects. However the only phenol derivative in widespread clinical use is the anaesthetic propofol (2,6-di-isopropylphenol).

Key features of anaesthesia are loss of consciousness, immobility in the presence of painful stimuli and absence of recall. Anaesthetics, such as propofol, are understood to mediate their anaesthetic effect by activating γ-aminobutyric acid ($GABA_A$) receptors in the Central Nervous System (CNS).

Analgesia is defined as the relief of pain. Among other peripheral and/or central nervous mechanisms, analgesia can arise as a result of enhanced inhibitory synaptic transmission within the dorsal horn of the spinal chord. It is understood that inhibitory postsynaptic transmission in the spinal chord involves mainly glycine receptors. Accordingly the glycine receptor family represents a target site for therapeutic agents aiming at inhibiting pain.

Both, $GABA_A$ and glycine receptors belong to the ligand-gated ion channel superfamily. They have a common structure in which five subunits form an ion channel. α and ß subunits assemble into a pentameric receptor with a proposed in vivo stochiometry of 3α: 2ß. Glycine receptors, like $GABA_A$ receptors, inhibit neuronal firing by opening chloride channels following agonist binding. Glycine receptors are mainly found in lower areas of the central nervous system and are involved in the control of motor rhythm generation, the coordination of spinal nociceptive reflex responses and the processing of sensory signals.

Chronic pain is very different from acute pain. Acute pain can be considered as a useful early warning system informing us about noxious stimuli and thereby helping us to escape and prevent damage. Chronic pain, in contrast, is a disease in its own right. Experts regard it as a dys-equilibrium syndrome, where inhibitory neuronal activity which under normal circumstances suppresses the processing of pain is markedly reduced. Treatment of chronic inflammatory or neuropathic pain is still difficult, and there is currently no single treatment that works for all conditions.

Increased neuronal excitability seen in chronic pain involves a loss of inhibition mediated by GABA- and/or glycinergic neurons in the superficial dorsal horn of the spinal cord that control the relay of nociceptive signals from the periphery to higher areas of the central nervous system. In the adult dorsal horn, the contribution of glycine to fast inhibitory postsynaptic transmission dominates. Glycine receptors are mainly found in lower areas of the central nervous system and are involved in the control of motor rhythm generation, the coordination of spinal nociceptive reflex responses and the processing of sensory signals. Their role in modulating ascending nociceptive pathways and pain makes them a potentially interesting target site for analgesic and spasmolytic agents. Microinjection of the glycine receptor agonist taurine into the anterior cingulate cortex—associated with the affective component of pain—relieves neuropathic pain, an effect that could be antagonized by the selective glycine receptor antagonist strychnine. There are four α-subunits and one ß-subunit for the strychnine-sensitive glycine receptor, the α1-subunit is widely expressed in the adult spinal cord and brain stem, but also in higher centres of the brain involved in sensory processing. The glycine receptor α3-subunit has been identified as a target site underlying central inflammatory pain sensitization due to $PGE_2$-induced receptor phosphorylation. α3-subunit knock-out mice do not develop inflammatory pain with otherwise normal response to acute pain. This phenomenon may be explained by the fact that α1 containing glycine receptor subunits which probably compensate for the lack in α3 do not possess the protein kinase A (PKA) phosphorylation site involved in the $PGE_2$ signal transduction. Furthermore, phosphorylation of the α3 subunit is not necessarily involved in neuropathic pain. Based on this understanding, a need has been identified by the inventors for the development of drugs that target the predominant adult glycine receptor isoform containing the α1 subunit. Given the physiological role of glycine receptors and their relatively restricted expression (mainly in the spinal cord and lower brain areas), a selective glycine modulator should be of great interest therapeutically to increase inhibition at the level of the spinal cord dorsal horn.

There exists a need to develop new and improved analgesics. Despite that fact that glycine receptors represent a good target for identifying such analgesics, there are no existing analgesics that effectively target these receptors. The inventors therefore decided to address this issue and exploited their knowledge of the pathophysiological mechanisms underlying anaesthesia and analgesia with a view to identifying new and improved drugs for controlling pain.

Aspects of the invention were devised with the foregoing in mind.

SUMMARY OF THE INVENTION

In one aspect, the present invention provides a compound, or a pharmaceutically acceptable salt or solvate thereof, as defined herein.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a disease or condition in which the selective, positive allosteric modulation of strychnine-sensitive alpha 1-glycine receptors is beneficial.

In a particular aspect, the present invention provides a compound as defined herein, or a pharmaceutically acceptable salt or solvate thereof, or a pharmaceutical composition as defined herein, for use in the treatment of pain. In a particular embodiment, the pain is present in a human subject.

In a particular aspect, the present invention provides a compound as defined herein, or a pharmaceutically acceptable salt or solvate thereof, or a pharmaceutical composition as defined herein, for use in the treatment of chronic pain. In a particular embodiment, the chronic pain is present in a human subject.

In a particular aspect, the present invention provides a compound as defined herein, or a pharmaceutically acceptable salt or solvate thereof, or a pharmaceutical composition as defined herein, for use in the treatment of neuropathic pain. In a particular embodiment, the chronic pain is present in a human subject.

In another aspect, the present invention provides a compound as defined herein, or a pharmaceutically acceptable salt or solvate thereof, or a pharmaceutical composition as defined herein, for use in the selective, positive allosteric modulation of strychnine-sensitive alpha 1-glycine receptors.

In another aspect, the present invention provides the use of a compound as defined herein, or a pharmaceutically acceptable salt or solvate thereof, in the manufacture of a medicament for use in the treatment of a disease or condition in which the selective, positive allosteric modulation of strychnine-sensitive alpha 1-glycine receptors is beneficial.

In a particular aspect, the present invention provides the use of a compound as defined herein, or a pharmaceutically acceptable salt or solvate thereof, in the manufacture of a medicament for use in the treatment of pain. Suitably, the medicament is for use in the treatment of pain in a human subject.

In a particular aspect, the present invention provides the use of a compound as defined herein, or a pharmaceutically acceptable salt or solvate thereof, in the manufacture of a medicament for use in the treatment of chronic pain. Suitably, the medicament is for use in the treatment of chronic pain in a human subject.

In a particular aspect, the present invention provides the use of a compound as defined herein, or a pharmaceutically acceptable salt or solvate thereof, in the manufacture of a medicament for use in the treatment of neuropathic pain. In a particular embodiment, the neuropathic pain is present in a human subject.

In another aspect, the present invention provides the use of a compound as defined herein, or a pharmaceutically acceptable salt or solvate thereof, in the manufacture of a medicament for use in the selective, positive allosteric modulation of strychnine-sensitive alpha 1-glycine receptors.

In another aspect, the present invention provides a method of selectively producing a positive allosteric modulation effect in strychnine-sensitive alpha 1-glycine receptors in vitro or in vivo, said method comprising contacting a cell with an effective amount of a compound as defined herein, or a pharmaceutically acceptable salt or solvate thereof.

In another aspect, the present invention provides a method of treating a disease or condition in which the selective, positive allosteric modulation of strychnine-sensitive alpha 1-glycine receptors is beneficial in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating pain in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating chronic pain in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating neuropathic pain in a patient in need of such treatment, said method comprising administering to said patient a therapeutically effective amount of a compound as defined herein, or a pharmaceutically acceptable salt or solvate thereof, or a pharmaceutical composition as defined herein.

The present invention further provides a method of synthesising a compound as defined herein, or a pharmaceutically acceptable salt or solvate thereof.

In another aspect, the present invention provides a compound as defined herein, or a pharmaceutically acceptable salt or solvate thereof, obtainable by, or obtained by, or directly obtained by any one of the methods of synthesis defined herein.

In another aspect, the present invention provides novel intermediates defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "halo" refers to fluoro, chloro, bromo and iodo.

The phrase "compound of the invention" means those compounds which are disclosed herein, both generically and specifically.

Compounds of the Invention

In one aspect, the present invention provides a compound of formula I shown below:

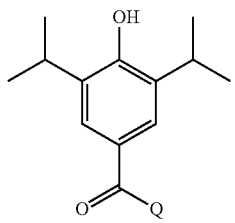

(I)

wherein:
Q is selected from:

(i)

(ii)

(iii)

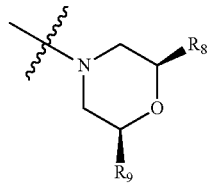

(iv)

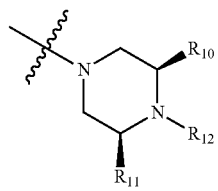

(v)

wherein:
$R_1$, $R_{2a}$, $R_{2b}$ and $R_3$ are each independently selected from hydrogen, halo, methyl, hydroxymethyl, $CF_3$ and $OCF_3$; or $R_{2a}$ and $R_{2b}$ are linked such that together they form a 4, 5 or 6-membered carbocyclic or heterocyclic ring;

$R_4$ and $R_5$ are each independently selected from hydrogen, halo, methyl, hydroxymethyl, $CF_3$ and $OCF_3$;

$R_6$ and $R_7$ are each independently selected from hydrogen, halo, methyl, hydroxymethyl, $CF_3$ and $OCF_3$;

$R_8$ and $R_9$ are each independently selected from hydrogen, methyl, $CF_3$ halo, hydroxymethyl and $OCF_3$;

$R_{10}$ and $R_{11}$ are each independently selected from hydrogen, methyl, $CF_3$ halo, hydroxymethyl and $OCF_3$;

$R_{12}$ is selected from hydrogen, (1-4C)alkyl or (1-4C)haloalkyl;

or a pharmaceutically acceptable salt thereof.

In another aspect, the present invention provides a compound of formula I shown below:

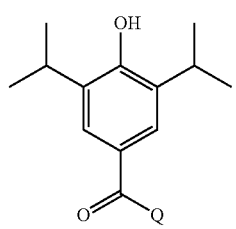

(I)

wherein:
Q is selected from:

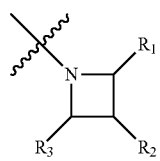

(i)

-continued

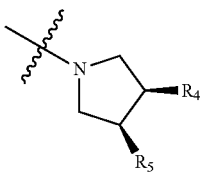
(ii)

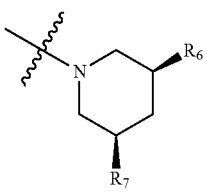
(iii)

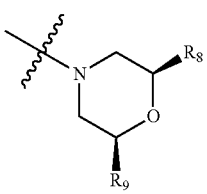
(iv)

wherein:
R₁, R₂ and R₃ are each independently selected from hydrogen, halo, methyl, hydroxymethyl, CF₃ and OCF₃;
R₄ and R₅ are each independently selected from hydrogen, halo, methyl, hydroxymethyl, CF₃ and OCF₃;
R₆ and R₇ are each independently selected from hydrogen, halo, methyl, hydroxymethyl, CF₃ and OCF₃;
R₈ and R₉ are each independently selected from hydrogen, methyl, CF₃ halo, hydroxymethyl and OCF₃;
or a pharmaceutically acceptable salt thereof.

In the compounds of formula I above, $\sim\!\sim\!\sim$ indicates the bond that attaches Q to the C(=O) moiety of the compound of formula I. In all cases, Q is a nitrogen linked heterocyclic ring of the formula (i), (ii), (iii), (iv) or (v) shown above.

Particular compounds of the invention include, for example, compounds of the formula I, or pharmaceutically acceptable salts or solvates thereof, wherein, unless otherwise stated, each of Q, R₁, R₂ₐ, R₂ᵦ, R₂, R₃, R₄, R₅, R₆, R₇, R₈, R₉, R₁₀, R₁₁ and R₁₂ has any of the meanings defined hereinbefore or in any one of paragraphs (1) to (33) hereinafter:—

(1) Q is selected from:

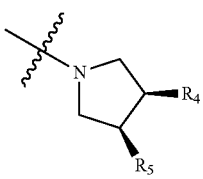
(ii)

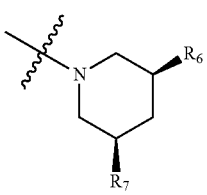
(iii)

-continued

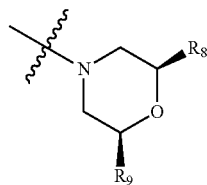
(iv)

(2) Q is selected from:

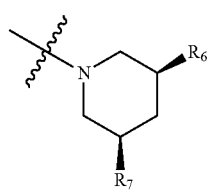
(iii)

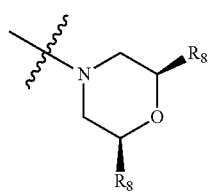
(iv)

(3) Q is:

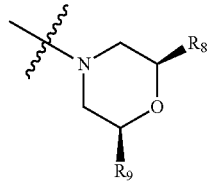
(iv)

(4) Q is of formula (i) and R₁, R₂, R₂ₐ, R₂ᵦ and R₃ are each independently selected from hydrogen, halo, methyl, hydroxymethyl, CF₃ and OCF₃; or R₂ₐ and R₂ᵦ are linked such that together they form a 4 or 5 membered carbocyclic or heterocyclic ring;

(5) Q is of formula (i) and one of R₂ₐ or R₂ᵦ is hydrogen and the other is selected from hydrogen, fluoro, methyl, hydroxymethyl, CF₃ and OCF₃; or R₂ₐ and R₂ᵦ are linked such that together they form a 4 membered heterocyclic ring comprising one N or O atom;

(6) R₁, R₂ₐ, R₂ᵦ and R₃ are each independently selected from hydrogen, fluoro, methyl, hydroxymethyl, CF₃ and OCF₃;

(7) R₁, R₂ₐ, R₂ᵦ and R₃ are each independently selected from hydrogen, fluoro, methyl, hydroxymethyl, CF₃ and OCF₃;

(8) R₁, R₂ₐ, R₂ᵦ and R₃ are each independently selected from hydrogen, fluoro or methyl;

(9) R₁, R₂ₐ, R₂ᵦ and R₃ are all hydrogen;

(10) one or two of R₁, R₂ₐ, R₂ᵦ, R₂ and R₃ is a substituent other than hydrogen;

(11) one of R₁, R₂ₐ, R₂ᵦ, R₂ and R₃ is a substituent other than hydrogen.

(12) R₁ and R₃ are each independently selected from hydrogen, fluoro or methyl and R₂ₐ and R₂ᵦ are hydrogen;

(13) $R_{2a}$ and $R_{2b}$ are hydrogen and one of $R_1$ and $R_3$ is selected from hydrogen, fluoro or methyl and the other is hydrogen;
(14) $R_1$, $R_{2a}$ and $R_3$ are hydrogen and $R_{2b}$ is selected from hydrogen, fluoro, methyl, hydroxymethyl, $CF_3$ and $OCF_3$;
(15) $R_1$, $R_{2a}$ and $R_3$ are hydrogen and $R_{2b}$ is fluoro;
(16) $R_1$ and $R_3$ are hydrogen and $R_{2a}$ and $R_{2b}$ are linked such that together they form a 4 membered carbocyclic or heterocyclic ring;
(17) $R_4$ and $R_5$ are each independently selected from hydrogen, fluoro, methyl, hydroxymethyl, $CF_3$ and $OCF_3$;
(18) $R_4$ and $R_5$ are each independently selected from hydrogen, fluoro or methyl;
(19) $R_4$ and $R_5$ are both hydrogen;
(20) one of $R_4$ and $R_5$ is fluoro or methyl and the other is hydrogen;
(21) $R_6$ and $R_7$ are each independently selected from hydrogen, fluoro, methyl, hydroxymethyl, $CF_3$ and $OCF_3$;
(22) $R_6$ and $R_7$ are each independently selected from hydrogen, fluoro or methyl;
(23) $R_6$ and $R_7$ are both hydrogen;
(24) one of $R_6$ and $R_7$ is fluoro or methyl and the other is hydrogen.
(25) $R_8$ and $R_9$ are each independently selected from hydrogen or methyl;
(26) $R_8$ and $R_9$ are both hydrogen;
(27) one of $R_8$ and $R_9$ is methyl and the other is hydrogen;
(28) $R_{10}$ and $R_{11}$ are each independently selected from hydrogen, fluoro or methyl;
(29) $R_{10}$ and $R_{11}$ are both hydrogen;
(30) one of $R_{10}$ and $R_{11}$ is methyl and the other is hydrogen;
(31) $R_{10}$ and $R_{11}$ are both hydrogen and $R_{12}$ is methyl;
(32) $R_{12}$ is selected from hydrogen or (1-4C)alkyl;
(33) $R_{12}$ is methyl.

Suitably, Q is as defined in paragraphs (1), (2) or (3) above. In an embodiment, Q has the structural formula (i). In another embodiment, Q has the structural formula (ii). In an embodiment, Q has the structural formula (iii). In a particular embodiment, Q has the structural formula (iv).

In a particular embodiment, Q is as defined in paragraph (3) above.

Suitably when Q is of formula (i), it has the formula shown below:

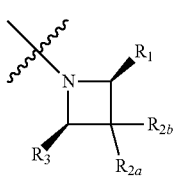

(i)

Suitably, $R_1$, $R_{2a}$, $R_{2b}$ and $R_3$ are as defined in any one of paragraphs (4) to (16) above.

Suitably, $R_4$ and $R_5$ are as defined in any one of paragraphs (17) to (20) above. In a particular embodiment, $R_4$ and $R_5$ are as defined in paragraph (20) above.

Suitably, $R_6$ and $R_7$ are as defined in any one of paragraphs (21) to (24) above. In a particular embodiment, $R_6$ and $R_7$ are as defined in paragraph (23) or (24) above.

Suitably, $R_8$ and $R_9$ are as defined in any one of paragraphs (25) to (27) above. In a particular embodiment, $R_6$ and $R_7$ are as defined in paragraph (26) or (27) above.

Suitably, $R_{10}$ and $R_{11}$ are as defined in any one of paragraphs (28) to (30) above. In a particular embodiment, $R_6$ and $R_7$ are as defined in paragraph (29) or (30) above.

In a particular group of compounds of the invention, Q is of the structural formula (iv) shown above. Such compounds have the structural formula IA below:

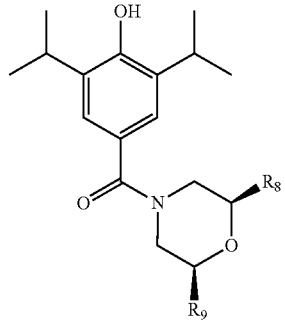

IA wherein $R_8$ and $R_9$ each have any one of the definitions set out herein.

In an embodiment of the compounds of formula IA, $R_8$ and $R_9$ are each independently selected from hydrogen or methyl.

In a further embodiment of the compounds of formula IA, $R_8$ and $R_9$ are both hydrogen.

In a further embodiment of the compounds of formula IA, one of $R_8$ and $R_9$ is methyl and the other is hydrogen.

Particular compounds of the invention include any one of the following:
  (4-(hydroxy)-3,5-diisopropylphenyl)(morpholino)methanone;
  (R)-(4-(hydroxy)-3,5-diisopropylphenyl)(2-methylmorpholino)methanone;
  (3-fluoroazetidin-1-yl) (4-hydroxy-3,5-diisopropyl phenyl) methanone;
  (4-(benzyloxy)-3,5-diisopropylphenyl)(piperidin-1-yl) methanone;
  (4-(hydroxy)-3,5-diisopropylphenyl)(morpholino)methanone;
  (4-Hydroxy-3,5-diisopropylphenyl)(2-oxa-6-azaspiro [3.3]heptan-6-yl) methanone;
  (4-Hydroxy-3-5-diisopropylphenyl)(4-methylpiperazin-1-yl)methanone;
or a pharmaceutically acceptable salt or solvate thereof.

In a particular embodiment, the compounds of the invention is:
  (4-(hydroxy)-3,5-diisopropylphenyl) (morpholino) methanone,
or a pharmaceutically acceptable salt or solvate thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess activity.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the invention may exist in solvated as well as unsolvated forms such as, for example, hydrated forms. It is to be understood that the invention encompasses all such solvated forms that possess activity.

It is also to be understood that certain compounds of the invention may exhibit polymorphism, and that the invention encompasses all such forms that possess activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

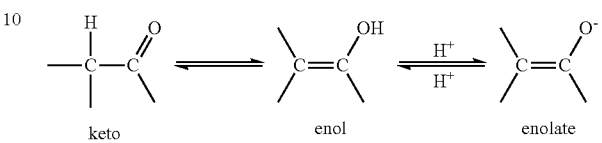

keto  enol  enolate

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);

b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

The compounds of the invention can be synthesised using chemistry techniques that are known in the art.

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

In a particular aspect, the present invention provides a method of synthesising a compound of the formula I, or a pharmaceutically acceptable salt or solvate thereof, the method comprising:

a) reacting a compound of formula A

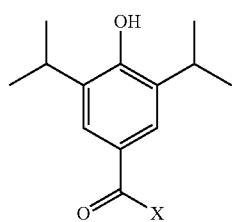

A wherein X is a reactive group, such as chloro; and the hydroxyl group is optionally protected;

with a compound of formula B:

H-Q wherein Q is as defined hereinbefore and the H atom is attached to a nitrogen atom of the Q group; and b) optionally thereafter, and if necessary:
   i) removing any protecting groups present;
   ii) converting the compound formula I into another compound of formula I; and/or
   iii) forming a pharmaceutically acceptable salt or solvate thereof.

X may be any suitable reactive group. Suitably X is a halogen, such as chlorine.

Suitably the coupling reaction between compound A and compound B takes place in the presence of a suitable solvent. Any suitable solvent or solvent mixture may be used for this reaction. A person skilled in the art will know how to select suitable solvents or solvent mixtures for use in these reactions. An example of a suitable solvent is dichloromethane.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out at room temperature or at an elevated temperature.

The compound of formula A can be prepared by processes known in the art, and suitably by the processes described herein with reference to the examples.

The compound of formula B can be prepared by processes known in the art, and suitably by the processes described herein with reference to the examples.

The resultant compound of formula I can be isolated and purified using techniques well known in the art.

The processes defined herein may further comprise the step of subjecting the compound of formula I to a salt exchange, particularly in situations where the compound of formula I is formed as a mixture of different salt forms. The salt exchange suitably comprises immobilising the compound of formula I on a suitable solid support or resin, and eluting the compounds with an appropriate acid to yield a single salt of the compound of formula I.

In a further aspect of the invention, there is provided a compound of formula I obtainable by any one of the processes defined herein.

In a further aspect of the invention, there is provided a compound of formula I obtained by any one of the processes defined herein.

In a further aspect of the invention, there is provided a compound of formula I directly obtained by any one of the processes defined herein.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In one aspect, the present invention provides a compound of formula I, or a pharmaceutically acceptable salt or solvate thereof, or a pharmaceutical composition as defined herein, for use in therapy.

The compounds of the invention are capable of the selective, positive allosteric modulation of strychnine-sensitive alpha 1-glycine receptors. As will be evident from the example section, the compounds of the invention target the glycine receptor α1-subunit, which is known to be positively modulated by anaesthetics, alcohols and cannabinoids, but the compounds according to the present invention selectively target this receptor family with high affinity.

In another aspect, the present invention provides a compound as defined herein, or a pharmaceutically acceptable salt or solvate thereof, or a pharmaceutical composition as defined herein, for use in the treatment of a disease or condition in which the selective, positive allosteric modulation of strychnine-sensitive alpha 1-glycine receptors is beneficial.

In a particular aspect, the present invention provides a compound as defined herein, or a pharmaceutically acceptable salt or solvate thereof, or a pharmaceutical composition as defined herein, for use in the treatment of pain. In a particular embodiment, the pain is present in a human subject.

In a particular aspect, the present invention provides a compound as defined herein, or a pharmaceutically acceptable salt or solvate thereof, or a pharmaceutical composition as defined herein, for use in the treatment of chronic pain, for example lower back pain or neuropathic pain. In a particular embodiment, the chronic pain is present in a human subject.

In a particular aspect, the present invention provides a compound as defined herein, or a pharmaceutically acceptable salt or solvate thereof, or a pharmaceutical composition as defined herein, for use in the treatment of neuropathic pain. In a particular embodiment, the neuropathic pain is present in a human subject.

In a particular aspect, the present invention provides a compound as defined herein, or a pharmaceutically acceptable salt or solvate thereof, or a pharmaceutical composition as defined herein, for use in the treatment of lower back pain. In a particular embodiment, the lower back pain is present in a human subject.

In another aspect, the present invention provides a compound as defined herein, or a pharmaceutically acceptable salt or solvate thereof, or a pharmaceutical composition as defined herein, for use in the selective, positive allosteric modulation of strychnine-sensitive alpha 1-glycine receptors.

In another aspect, the present invention provides the use of a compound as defined herein, or a pharmaceutically acceptable salt or solvate thereof, in the manufacture of a medicament for use in the treatment of a disease or condition in which the selective, positive allosteric modulation of strychnine-sensitive alpha 1-glycine receptors is beneficial.

In a particular aspect, the present invention provides the use of a compound as defined herein, or a pharmaceutically acceptable salt or solvate thereof, in the manufacture of a medicament for use in the treatment of pain. Suitably, the medicament is for use in the treatment of pain in a human subject.

In a particular aspect, the present invention provides the use of a compound as defined herein, or a pharmaceutically acceptable salt or solvate thereof, in the manufacture of a medicament for use in the treatment of chronic pain. Suitably, the medicament is for use in the treatment of chronic pain in a human subject.

In a particular aspect, the present invention provides the use of a compound as defined herein, or a pharmaceutically acceptable salt or solvate thereof, in the manufacture of a medicament for use in the treatment of neuropathic pain. In a particular embodiment, the neuropathic pain is present in a human subject.

In a particular aspect, the present invention provides the use of a compound as defined herein, or a pharmaceutically acceptable salt or solvate thereof, in the manufacture of a medicament for use in the treatment of lower back pain. In a particular embodiment, the lower back pain is present in a human subject.

In another aspect, the present invention provides the use of a compound as defined herein, or a pharmaceutically acceptable salt or solvate thereof, in the manufacture of a medicament for use in the selective, positive allosteric modulation of strychnine-sensitive alpha 1-glycine receptors.

In another aspect, the present invention provides a method of selectively producing a positive allosteric modulation effect in strychnine-sensitive alpha 1-glycine receptors in vitro or in vivo, said method comprising contacting a cell with an effective amount of a compound as defined herein, or a pharmaceutically acceptable salt or solvate thereof.

In another aspect, the present invention provides a method of treating a disease or condition in which the selective, positive allosteric modulation of strychnine-sensitive alpha 1-glycine receptors is beneficial in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating pain in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating chronic pain in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating neuropathic pain in a patient in need of such treatment, said method comprising administering to said patient a therapeutically effective amount of a compound as defined herein, or a pharmaceutically acceptable salt or solvate thereof, or a pharmaceutical composition as defined herein.

Routes of Administration

The compounds of the invention or pharmaceutical composition comprising the active compound may be administered to a subject by any convenient route of administration, whether systemically/peripherally or topically (ie. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The compounds of the invention may be administered as a sole therapy in order to treat the diseases or conditions identified herein. Alternatively, the therapy may involve the administration of one or more additional therapeutic agents (in addition to a compound of the invention).

For example, the pain treatment defined hereinbefore may involve the use of a compound of the invention as a sole therapy or may involve, in addition to the compound of the invention, the administration of one or more additional analgesic and/or anti-inflammatory agents. Examples of suitable medicaments include non-steroidal anti-inflammatory drugs and opiate analgesics.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of pain (e.g. chronic pain) comprising a compound of the invention as defined hereinbefore, or a pharmaceutically acceptable salt or solvate thereof, and another medicament.

According to this aspect of the invention there is provided a combination suitable for use in the treatment of pain (e.g. chronic pain) comprising a compound of the invention as defined hereinbefore, or a pharmaceutically acceptable salt or solvate thereof, and another analgesic.

In a further aspect of the invention there is provided a compound of the invention or a pharmaceutically acceptable salt or solvate thereof, in combination with another medicament for the treatment of pain (e.g. chronic pain).

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof, another medicament (e.g. another analgesic) and a pharmaceutically acceptable diluent or carrier.

BRIEF DESCRIPTION OF THE DRAWINGS

The invention is described further in reference to the accompanying Figures, in which.

EXAMPLES

Figure 1:
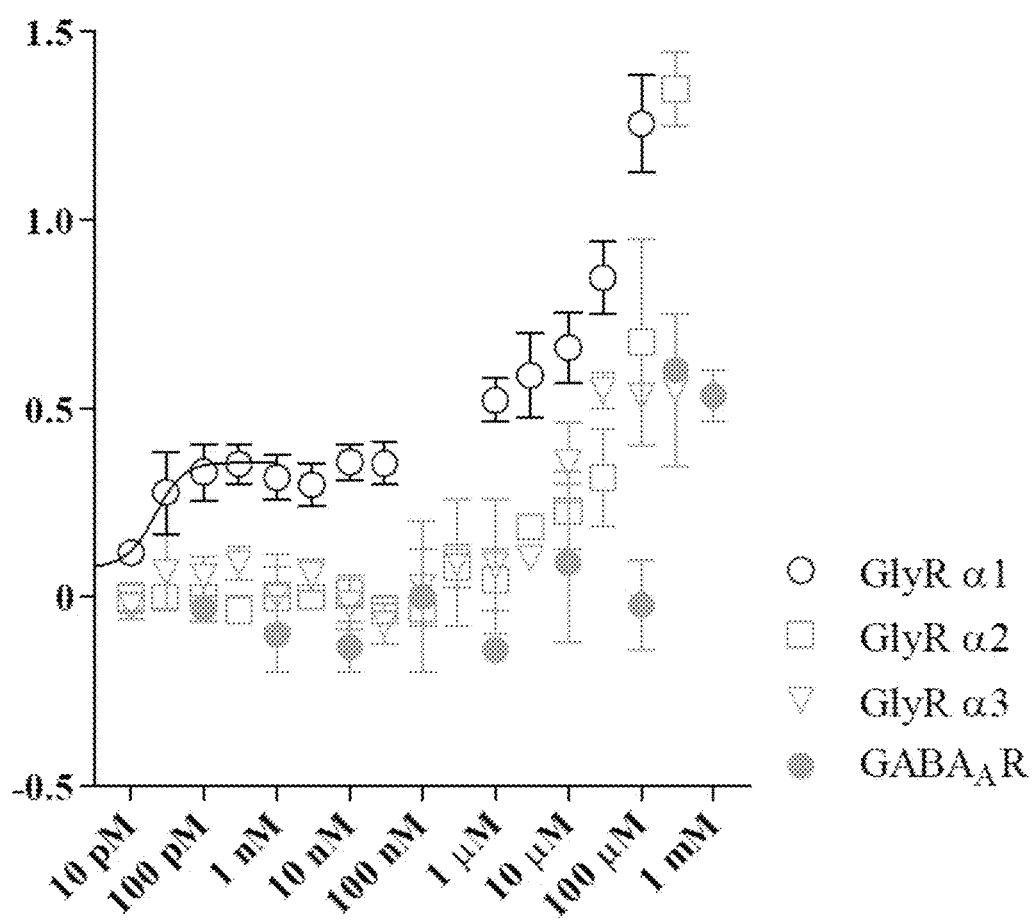
FIG. 1 shows the fractional potentiation (y-axis) against concentration (nM; x-axis) for the compound LT-01-25 in the expression and electrophysiology study described in Example 7 [Y axis: fractional potentiation—e.g. 0.75 mean that if a response to glycine alone was 1 μA then the response to glycine in the present of drug was 1.75 μA]

Example 1—Synthesis of (4-(hydroxy)-3,5-diisopropylphenyl)(morpholino)methanone (LT-01-25)

Step 1—Synthesis of 4-Hydroxy-3-5-diisopropylbenzaldehyde

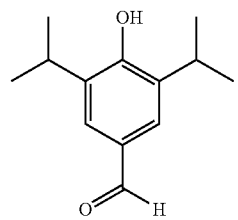

Hexamethylenetetramine (15.8 g, 56 mmol) was added to a solution of 2,6-Diisopropylphenol (10.4 mL) in glacial acetic acid (50 mL) and H$_2$O (10 mL). The resulting mixture was heated to reflux for 5 minutes and then short path distillation head was introduced and 10 ml of distillate was collected. The solution was allowed to continue refluxing for 6 hrs and the reaction was monitored by TLC. Upon completion of the reaction the solution was cooled to 00° C. and the resulting orange precipitation was isolated and washed with H$_2$O (3×50 mL) to afford product as a pale orange solid (10.3 g, 89% yield). $^1$H NMR (400 MHz, CDCl$_3$) δ 9.86 (s, 1H), 7.63 (s, 2H), 5.49 (s, 1H), 3.21 (m, 2H), 1.31 (d, J=6.9 Hz, 12H). MS: C$_{13}$H$_{18}$O$_2$ requires 206.3, found 206.3.

Step 2—Synthesis of 4-(benzyloxy)-3,5-diisopropylbenzaldehyde

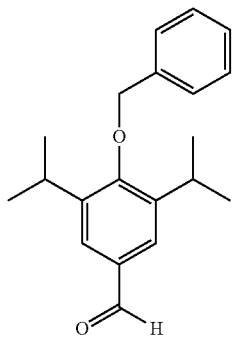 [SMILES: CC(C)c1cc(C=O)cc(C(C)C)c1OCc1ccccc1]

To a solution of 4-Hydroxy-3-5-diisopropylbenzaldehyde (4.18 g, 20.3 mmol) in acetone (50 mL) was added benzyl bromide (2.6 mL, 22.4 mmol) and potassium carbonate (5.6 g, 40.6 mmol). The resulting mixture was allowed to stir at room temperature for 18 hrs and the reaction was monitored by TLC. Upon completion the mixture was filtered through celite and the solvent was removed under vacuum. The product was purified by column chromatography (EtOAc/n-Hexane) to afford the product as an off white solid (5.3 g, 88% yield). $^1$H NMR (400 MHz, CDCl$_3$) δ 9.96 (s, 1H), 7.69 (s, 5H), 7.55-7.30 (m, 2H), 4.85 (s, 2H), 3.64-2.96 (m, 2H), 1.27 (d, J=6.9 Hz, 12H). MS: C$_{20}$H$_{24}$O$_2$ requires: 319.1679, found: 319.1674

Step 3—Synthesis of 4-(benzyloxy)-3,5-diisopropylbenzoic Acid

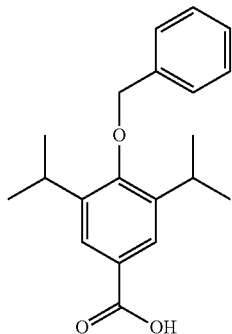 [SMILES: CC(C)c1cc(C(=O)O)cc(C(C)C)c1OCc1ccccc1]

4-(benzyloxy)-3,5-diisopropylbenzaldehyde (1.74 g, 5.87 mmol) was dissolved in THF (5 mL) under a blanket of N$_2$. Selenium dioxide (325 mg, 2.94 mmol) was added to the solution along with Hydrogen peroxide (1.5 mL, 27 wt %) and the mixture was heated to reflux for 18 hrs. Upon completion Pd/C (10 mg) was added and the reaction mixture was allowed to stir for 10 mins. The mixture was filtered through Celite™ and the solvent was removed under vacuum. The product was purified by column chromatography (EtOAc/n-Hexane) to afford the product as a white solid (1.6 g, 85% yield). $^1$H NMR (400 MHz, CDCl$_3$) δ 7.92 (s, 2H), 7.57-7.27 (m, 5H), 4.85 (s, 2H), 3.49-3.24 (m, 2H), 1.27 (d, J=6.9 Hz, 12H). MS [M+Na]$^+$: C$_{20}$H$_{24}$O$_3$ requires: 335.1625, found, 335.1623.

Step 4—Synthesis of 4-(benzyloxy)-3,5-diisopropylbenzoyl Chloride

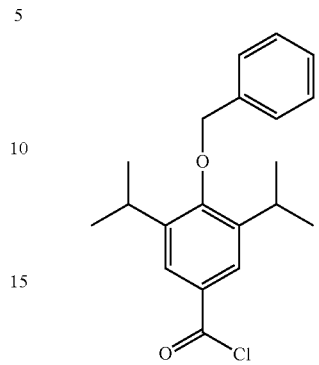

4-(benzyloxy)-3,5-diisopropylbenzoic acid (200 mg, 0.6 mmol) was dissolved in DCM (5 mL) under a blanket of N$_2$. Oxalyl chloride (0.12 mL, 0.72 mmol) was added along with DMF (1 drop from a pasture pipette). The reaction mixture was allowed to stir at room temperature for 2 hrs. The reaction was monitored by TLC and upon completion the solvent was removed under vacuum. The product was not isolated and was taken through crude.

Step 5—Synthesis of (4-(benzyloxy)-3,5-diisopropylphenyl)(morpholino)methanone

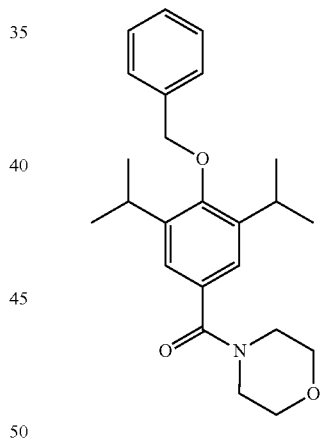

Morpholine (67 μL, 0.77 mmol) was added to a stirred solution of 4-(benzyloxy)-3,5-diisopropylbenzoyl chloride (200 mg, 0.64 mmol) in DCM (5 mL). Et$_3$N (133 μl, 9.6 mmol) was added and the resulting solution was allowed to stir at room temperature for 1.5 hours. The reaction was monitored by TLC and upon completion the reaction mixture was quenched with H$_2$O (50 mL) and extracted with EtOAc (3×50 mL). The combined organic extracts were washed with brine, dried over MgSO$_4$ and the solvent was removed under vacuum. The crude product was purified by column chromatography (EtOAc/n-Hexane) to afford the product as a white solid (192.9 mg 79% yield). $^1$H NMR (400 MHz, CDCl$_3$) δ 7.54-7.33 (m, 5H), 7.18 (s, 2H), 4.80 (s, 2H), 3.73 (s, 8H), 3.45-3.27 (m, 2H), 1.24 (d, J=6.9 Hz, 12H). MS [M+Na]+:C$_{24}$H$_{31}$NO$_3$ requires: 404.2202, found: 404.2196.

Step 6—Synthesis of (4-(benzyloxy)-3,5-diisopropylphenyl)(morpholino)methanone (LT-01-25)

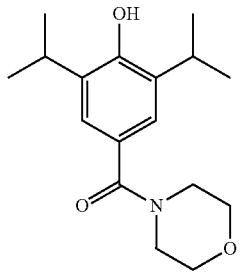 [SMILES: CC(C)c1cc(C(=O)N2CCOCC2)cc(C(C)C)c1O]

(4-(benzyloxy)-3,5-diisopropylphenyl)(morpholino)methanone (520 mg, 1.4 mmol) was dissolved in MeOH (10 mL) under a blanket of $H_2$. Pd/C (32 mg, 0.27 mmol) was added and the reaction mixture was allowed to stir for 18 hrs. Upon completion the reaction mixture was filtered through Celite™ and the solvent was removed under vacuum. The crude product was purified by column chromatography (EtOAc/n-Hexane) to afford the product as a white solid (346 mg, 85% yield). $^1$H NMR (400 MHz, CDCl$_3$) δ 7.14 (s, 2H), 5.06 (s, 1H), 3.71 (s, 8H), 3.15 (m, 2H), 1.26 (d, J=6.9 Hz, 12H). $^{13}$C NMR (101 MHz, CDCl$_3$) δ 171.74, 151.89, 134.12, 127.40, 123.58, 67.30, 27.47, 23.02. MS [M+Na]+: $C_{17}H_{25}NO_3$ requires: 314.1732, found: 314.1725 CHN requires C: 70.07%, H: 8.65%, N: 4.81%, found C: 69.05%, H: 8.54%, N: 4.71%.

Example 2—Synthesis of (R)-(4-(hydroxy)-3,5-diisopropylphenyl)(2-methylmorpholino)methanone Synthesis of 4-(benzyloxy)-3,5-diisopropylbenzoyl Chloride

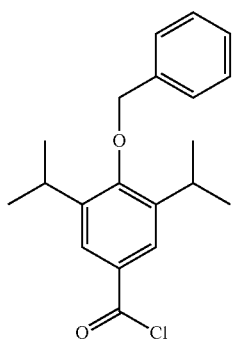 [SMILES: CC(C)c1cc(C(=O)Cl)cc(C(C)C)c1OCc1ccccc1]

4-(benzyloxy)-3,5-diisopropylbenzoic acid (200 mg, 0.6 mmol) was dissolved in DCM (5 mL) under a blanket of $N_2$. Oxalyl chloride (0.12 mL, 0.72 mmol) was added along with DMF (1 drop from a pasture pipette). The reaction mixture was allowed to stir at room temperature for 2 hrs. The reaction was monitored by TLC and upon completion the solvent was removed under vacuum. The product was not isolated and was taken through crude.

Synthesis of (R)-(4-(Benzyloxy)-3,5-diisopropylphenyl)(2-methylmorpholino)methanone

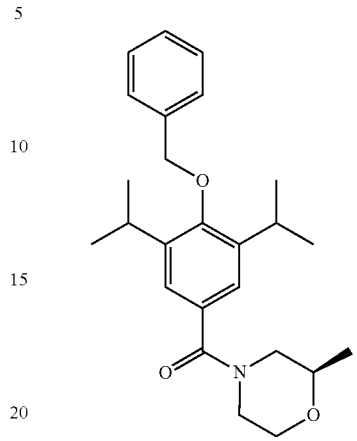

(R)-2-Mehtylmorpholine hydrochloride (164 mg, 1.19 mmol) was added to a stirred solution of 4-(benzyloxy)-3,5-diisopropylbenzoyl chloride (264 mg, 0.80 mmol) in DCM (5 mL). Et$_3$N (332 μl, 2.4 mmol) was added and the resulting solution was allowed to stir at room temperature for 1.5 hours. The reaction was monitored by TLC and upon completion the reaction mixture was quenched with $H_2O$ (50 mL) and extracted with EtOAc (3×50 mL). The combined organic extracts were washed with brine, dried over MgSO$_4$ and the solvent was removed under vacuum. The crude product was purified by column chromatography (EtOAc/n-Hexane) to afford the product as a white solid (151.7 mg 48% yield). $^1$H NMR (400 MHz, CDCl$_3$) δ 7.42 (m, 5H), 7.18 (s, 2H), 4.81 (s, 2H), 4.07-3.48 (m, 4H), 3.39 (m, 2H), 2.96 (m, 2H), 1.24 (d, J=6.9 Hz, 12H), 1.14 (s, 3H).

Synthesis of (R)-(4-(hydroxy)-3,5-diisopropylphenyl)(2-methylmorpholino)methanone

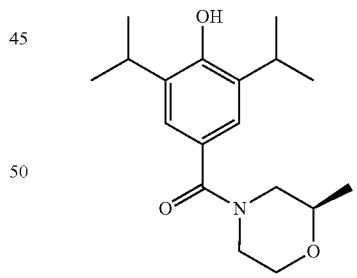

(4-(benzyloxy)-3,5-diisopropylphenyl)(morpholino)methanone (150 mg, 0.38 mmol) was dissolved in MeOH (10 mL) under a blanket of $H_2$. Pd/C (32 mg, 0.27 mmol) was added and the reaction mixture was allowed to stir for 18 hrs. Upon completion the reaction mixture was filtered through Celite™ and the solvent was removed under vacuum. The crude product was purified by column chromatography (EtOAc/n-Hexane) to afford the product as an off white solid (111 mg, 96% yield). $^1$H NMR (400 MHz, CDCl$_3$) δ 7.13 (s, 2H), 5.17 (s, 1H), 3.74 (d, J=127.9 Hz, 4H), 3.22-3.07 (m, 2H), 2.74 (s, 1H), 1.26 (d, J=6.8 Hz, 12H), 1.18 (s, 3H). $^{13}$C NMR (101 MHz, CDCl$_3$) δ 171.43, 152.11, 134.14, 126.52, 123.21, 72.14, 66.68, 26.88, 22.68, 18.61. MS [M+Na]$^+$:C$_{18}$H$_{27}$NO$_3$ requires: 328.1899, found: 328.1889. CHN requires C: 70.79%, H: 8.91%, N: 4.59%, found C: 70.56%, H: 8.55%, N: 4.61%

Example 3—Synthesis of (3-Fluoroazetidin-1-yl)(4-hydroxy-3,5-diisopropylphenyl)methanone Synthesis of 4-(benzyloxy)-3,5-diisopropylphenyl)(3-fluoroazetidin-1-yl)methanone

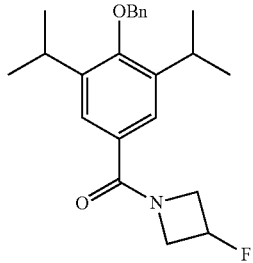 [SMILES: CC(C)c1cc(C(=O)N2CC(F)C2)cc(C(C)C)c1OCc1ccccc1]

3-Fluoroazetidine hydrochloride (2500 mg, 2.25 mmol) was added to a stirred solution of 4-(benzyloxy)-3,5-diisopropylbenzoyl chloride (prepared as described in Example 1; 500 mg, 1.5 mmol) in DCM (5 mL). Et$_3$N (597 µl, 4.5 mmol) was added and the resulting solution was allowed to stir at room temperature for 1.5 hours. The reaction was monitored by TLC and upon completion the reaction mixture was quenched with H$_2$O (50 mL) and extracted with EtOAc (3×50 mL). The combined organic extracts were washed with brine, dried over MgSO$_4$ and the solvent was removed under vacuum. The crude product was purified by column chromatography (EtOAc/n-Hexane) to afford the product as a white solid (387.4 mg 70% yield). $^1$H NMR (400 MHz, CDCl$_3$) δ 7.53-7.34 (m, 6H), 5.36 (dddd, J=56.8, 9.6, 6.2, 3.5 Hz, 1H), 4.58-4.46 (m, 2H), 4.45-4.30 (m, 2H), 3.44-3.33 (m, 2H), 1.24 (d, J=6.9 Hz, 12H).

Synthesis of (3-Fluoroazetidin-1-yl)(4-hydroxy-3,5-diisopropylphenyl)methanone

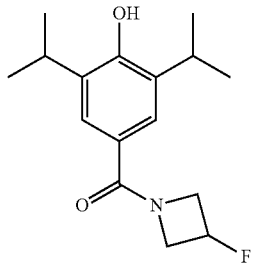 [SMILES: CC(C)c1cc(C(=O)N2CC(F)C2)cc(C(C)C)c1O]

4-(benzyloxy)-3,5-diisopropylphenyl)(3-fluoroazetidin-1-yl)methanone (387 mg, 1.05 mmol) was dissolved in MeOH (10 mL) under a blanket of H$_2$. Pd/C (32 mg, 0.27 mmol) was added and the reaction mixture was allowed to stir for 18 hrs. Upon completion the reaction mixture was filtered through Celite™ and the solvent was removed under vacuum. The crude product was purified by column chromatography (EtOAc/n-Hexane) to afford the product as a white solid (223 mg, 76% yield)$^1$H NMR (400 MHz, CDCl$_3$) δ 7.36 (s, 2H), 5.66 (s, 1H), 5.36 (dddd, J=56.8, 9.6, 6.2, 3.5 Hz, 1H), 4.58-4.26 (m, 4H), 3.26-3.12 (m, 2H), 1.25 (d, J=6.9 Hz, 12H). MS [M+H]$^+$:C$_{16}$H$_{22}$FNO$_3$ requires: 280.1711, found: 280.1707.

Example 4—Synthesis of (4-(Benzyloxy)-3,5-diisopropylphenyl)(piperidin-1-yl)methanone Synthesis of 4-(benzyloxy)-3,5-diisopropylbenzoyl Chloride

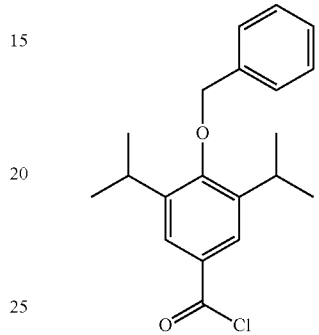

4-(benzyloxy)-3,5-diisopropylbenzoic acid (200 mg, 0.6 mmol) was dissolved in DCM (5 mL) under a blanket of N$_2$. Oxalyl chloride (0.12 mL, 0.72 mmol) was added along with DMF (1 drop from a pasture pipette). The reaction mixture was allowed to stir at room temperature for 2 hrs. The reaction was monitored by TLC and upon completion the solvent was removed under vacuum. The product was not isolated and was taken through crude.

Synthesis of (4-(Benzyloxy)-3,5-diisopropylphenyl)(piperidin-1-yl)methanone

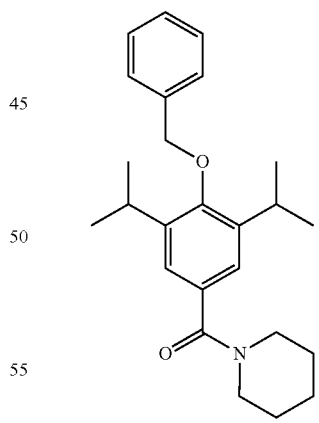

Piperidine (230 µL, 2.25 mmol) was added to a stirred solution of 4-(benzyloxy)-3,5-diisopropylbenzoyl chloride (500 mg, 1.5 mmol) in DCM (5 mL). Et$_3$N (310 µl, 2.25 mmol) was added and the resulting solution was allowed to stir at room temperature for 1.5 hours. The reaction was monitored by TLC and upon completion the reaction mixture was quenched with H$_2$O (50 mL) and extracted with EtOAc (3×50 mL). The combined organic extracts were washed with brine, dried over MgSO$_4$ and the solvent was removed under vacuum. The crude product was purified by column chromatography (EtOAc/n-Hexane) to afford the product as an off white solid (546 mg 95% yield). $^1$H NMR (400 MHz, CDCl$_3$) δ 7.52-7.32 (m, 5H), 7.16 (s, 2H), 4.80 (s, 1H), 3.71 (s, 4H), 3.35-3.45 (m, 2H), 1.64 (d, J=43.1 Hz, 6H), 1.23 (d, J=6.9 Hz, 12H). [M+H]$^+$:C$_{25}$H$_{34}$NO$_2$ requires: 380.2590, found: 380.2575

Synthesis of (4-hydroxy-3,5-diisopropylphenyl)(piperidine-1-yl)methanone

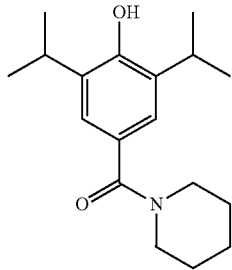 [SMILES: CC(C)c1cc(C(=O)N2CCCCC2)cc(C(C)C)c1O]

(4-hydroxy-3,5-diisopropylphenyl)(piperidine-1-yl)methanone (520 mg, 1.40 mmol) was dissolved in MeOH (10 mL) under a blanket of H$_2$. Pd/C (32 mg, 0.27 mmol) was added and the reaction mixture was allowed to stir for 18 hrs. Upon completion the reaction mixture was filtered through Celite™ and the solvent was removed under vacuum. The crude product was purified by column chromatography (EtOAc/n-Hexane) to afford the product as an off white solid (323 mg, 80% yield). $^1$H NMR (400 MHz, CDCl$_3$) δ 7.12 (s, 2H), 4.97 (s, 1H), 3.50 (s, 4H), 3.20-3.08 (m, 2H), 1.64 (d, J=33.5 Hz, 1H), 1.26 (d, J=6.9 Hz, 1H). MS [M+Na]$^+$:C$_{18}$H$_{28}$NO$_2$ requires: 290.2120, found: 290.2123.

Example 5—Synthesis of (4-Hydroxy-3,5-diisopropylphenyl)(2-oxa-6-azaspiro[3.3]heptan-6-yl)methanone Synthesis of 4-Hydroxy-3-5-diisopropylbenzoic Acid

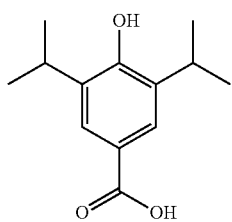

NaClO$_2$ (1.3 g, 14.4 mmol) was added to a solution of 4-Hydroxy-3-5-diisopropylbenzaldehyde (1.0 g, 4.8 mmol) NaH$_2$PO$_4$ (2.2 g, 14.4 mmol) and 2-methyl-2-butene (9.5 mL, 2M in THF) in BuOH/H$_2$O (1:1, 15 mL). The reaction was allowed to stir at room temperature for 16 hours. Upon completion the reaction mixture was diluted with Na$_2$CO$_3$ (50 mL) and was washed with EtOAc (50 mL). The aqueous layer was acidified to pH 1 (20 mL HCl, 1 M) and extracted with EtOAc (3×30 mL). The organic extracts were collected and dried over MgSO$_4$ and concentrated under vacuum to afford the product. The product was purified column chromatography (EtOAc/n-Hexane) to give the product as a white solid (739 mg, 68% yield). $^1$H NMR (400 MHz, CDCl$_3$) δ 7.85 (s, 2H), 5.30 (s, 1H), 3.21-3.11 (m, 2H), 1.30 (d, J=6.8 Hz, 12H). $^{13}$C NMR (101 MHz, CDCl$_3$) δ 172.25, 155.07, 133.42, 126.77, 121.39, 27.27, 22.45.MS: C13H18O3 [M+NH$_4$]$^+$ requires 240.2, found 240.2.

Synthesis of 4-(benzyloxy)-3,5-diisopropylbenzoic Acid

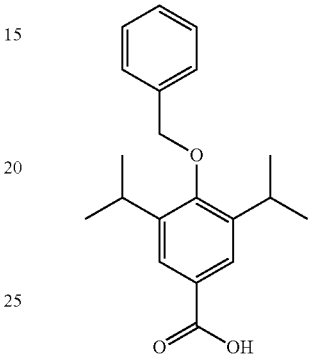

4-(benzyloxy)-3,5-diisopropylbenzaldehyde (1.74 g, 5.87 mmol) was dissolved in THF (5 mL) under a blanket of N$_2$. Selenium dioxide (325 mg, 2.94 mmol) was added to the solution along with hydrogen peroxide (1.5 mL, 27 wt %) and the mixture was heated to reflux for 18 hours. Upon completion Pd/C (10 mg) was added and the reaction mixture was allowed to stir for 10 mins. The mixture was filtered through Celite™ and the solvent was removed under vacuum. The product was purified by column chromatography (EtOAc/n-Hexane) to afford the product as a white solid (1.6 g, 85% yield). $^1$H NMR (400 MHz, CDCl$_3$) δ 7.92 (s, 2H), 7.57-7.27 (m, 5H), 4.85 (s, 2H), 3.40 (hept, J=6.8 Hz, 2H), 1.27 (d, J=6.8 Hz, 12H). $^{13}$C NMR (101 MHz, CDCl$_3$) δ 171.53, 158.06, 142.57, 137.06, 128.65, 128.19, 127.43, 126.77, 125.49, 76.51, 26.76, 23.93. MS [M+Na]$^+$: C$_{20}$H$_{24}$O$_3$ requires: 335.1625, found: 335.1623

Synthesis of (4-(Benzyloxy)-3,5-diisopropylphenyl)(2-oxa-6-azaspiro[3.3]heptan-6-yl)methanone

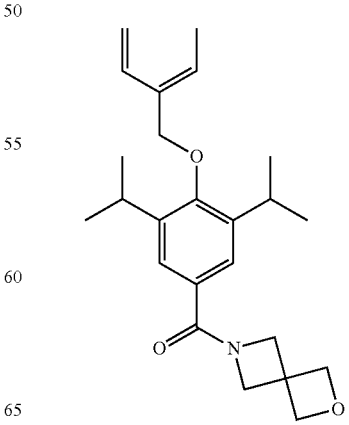

To a solution of 4-(benzyloxy)-3,5-diisopropylbenzoic acid (100 mg, 0.32 mmol) in DMF (5 mL) was added HATU (180, 0.48 mmol), $K_2CO_3$ (220 mg, 1.6 mmol) and 2-oxa-6-azaspiro[3.3]heptan-6-ium carboxyformate (101 mg, 0.35 mmol). The resulting solution was allowed to stir for 1 hour. Upon completion the reaction mixture was quenched with $H_2O$ (20 mL) and extracted with EtOAc (3×30 mL). The combined organic extracts were washed with $H_2O$ (3×30 mL), brine (20 mL), dried over $MgSO_4$ and the solvent was removed under vacuum. The crude product was purified by column chromatography (EtOAc/n-Hexane) to afford the product as a white solid (62 mg, 50% yield). $^1$H NMR (400 MHz, $CDCl_3$) δ 7.54-7.31 (m, 7H), 4.83 (d, J=11.7 Hz, 6H), 4.40 (d, J=42.4 Hz, 4H), 3.39 (hept, J=6.8 Hz, 2H), 1.25 (d, J=6.8 Hz, 12H). $^{13}$C NMR (101 MHz, $CDCl_3$) δ 170.82, 157.83, 142.63, 128.66, 128.31, 127.37, 126.60, 125.44, 72.92, 60.89, 53.37, 26.39, 24.02. MS [M+Na]+: $C_{25}H_{31}NO_3$ requires: 416.2202, found: 416.2186.

Synthesis of (4-Hydroxy-3,5-diisopropylphenyl)(2-oxa-6-azaspiro[3.3]heptan-6-yl)methanone

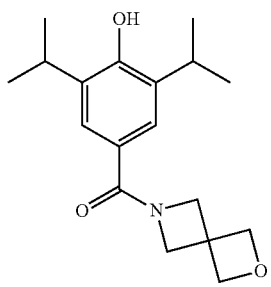 [SMILES: CC(C)c1cc(C(=O)N2CC3(COC3)C2)cc(C(C)C)c1O]

(4-(Benzyloxy)-3,5-diisopropylphenyl)(2-oxa-6-azaspiro[3.3]heptan-6-yl)methanone (50 mg, 0.13 mmol) was reacted with Pd/C (15 mg, 0.12 mmol) according to the procedure described in paragraph [00163]. The crude product was purified by column chromatography (EtOAc/n-Hexane) to afford the product as a white solid (38 mg, 99% yield) $^1$H NMR (400 MHz, $CDCl_3$) δ 7.35 (s, 2H), 5.43 (s, 1H), 4.82 (s, 4H), 4.39 (d, J=41.9 Hz, 4H), 3.16 (hept, J=6.8 Hz, 2H), 1.26 (d, J=6.8 Hz, 12H). $^{13}$C NMR (101 MHz, $CDCl_3$) δ 172.27, 154.00, 134.78, 125.74, 125.05, 82.10, 39.57, 28.22, 23.79. MS [M+H]+:$C_{18}H_{26}NO_3$ requires: 304.1907, found: 304.1906. CHN requires C: 71.26%, H: 8.31%, N: 4.62%, found C: 71.12%, H: 8.16%, N: 4.38%

Example 6—Synthesis of (4-Hydroxy-3-5-diisopropylphenyl)(4-methylpiperazin-1-yl)methanone

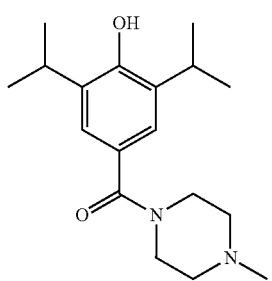 [SMILES: CC(C)c1cc(C(=O)N2CCN(C)CC2)cc(C(C)C)c1O]

4-Hydroxy-3-5-diisopropylbenzoyl chloride (160 mg, 0.66 mmol) was reacted with N-methylpiperazine (0.088 mL, 0.80 mmol) according to general procedure 1 (below) to afford the product as a brown solid. The crude product was purified by trituration with EtOAc (109 mg, 55% yield). m.p.=154-156° C.: $^1$H NMR (400 MHz, $CDCl_3$) δ 7.13 (s, 2H), 5.18 (s, 1H), 3.74 (s, 4H), 3.16 (hept, J=6.8 Hz, 2H), 2.44 (s, 4H), 1.26 (d, J=6.8 Hz, 12H). $^{13}$C NMR (101 MHz, $CDCl_3$) δ 171.24, 151.59, 133.65, 127.18, 123.19, 65.87, 54.82, 45.78, 27.12, 22.62. MS: $C_{18}H_{28}N_2O_2$ requires: 305.2229, found: 305.2224. CHN requires C: 71.02%, H: 9.27%, N: 9.20%, found C: 68.44%, H: 9.03%, N: 8.39%.

General Procedure 1—Amide Coupling

The appropriate morpholine derivative (1.2 eq) was added to a stirred solution of the acid chloride (1.0 eq) dissolved in DCM (10 mL/g). $Et_3N$ (1.5 eq) was added and the resulting solution was allowed to stir at room temperature for 1.5 hours. The reaction was monitored by TLC and upon completion the reaction mixture was quenched with $H_2O$ (50 mL) and extracted with EtOAc (3×50 mL). The combined organic extracts were washed with $Na_2CO_3$, dried over $MgSO_4$ and the solvent was removed under vacuum.

Example 7—Expression and Electrophysiological Characterization of Glycine and GABA Receptor Activity Human embryonic kidney (HEK) 293 cells (ATCC CRL 1573) and/or *Xenopus laevis* oocytes were used for expressing the human α1-3 glycine receptor subunit as well as human a1, b3, g2 GABA receptor subunit cDNAs inserted into mammalian expression vectors. Patch- and voltage-clamp recording from receptor expressing cells was performed at a holding potential of −70 mV in normal Ringer solution and digitized for analyses. Dose-response curves of agonist induced peak currents (I) were normalized to the maximal current value obtained and fitted with the sigmoidal Hill equation using a Gauss Marquardt iteration, where EC50 represents the glycine/GABA concentration resulting in a half maximal response. Effects of the compounds tested on agonist induced currents were analysed after superfusing the cells with the respective compound for 5 seconds prior to and during agonist application and dose-response curves of modulated currents were determined in the presence of agonist concentrations eliciting a response corresponding to 20% of the maximal inducible current (EC20 value). Results represent means±s.d. and the significance of the data was evaluated using Student's paired t test and considered to be statistically significant at $P<0.05$.

The results are shown in FIG. 1 for the compound of Example 1 (LT-01-25).

The following $EC_{50}$ data was obtained for the compounds of Examples 2 to 6:

| Compound | α1 glycine $EC_{50}$ (nM) |
| --- | --- |
| Example 2 | 0.06 +/− 0.01 |
| Example 3 | 0.43 +/− 0.28 |
| Example 5 | 0.00016 +/− 0.00004 |
| Example 6 | 0.0012 +/− 0.0004 |

Example 8—Biological Evaluation for LT-01-25 (Example 1)

(i) In Vivo Assessment of Paw Withdrawal Thresholds for LT-01-25 (Example 1)

Animals

All animal procedures were carried out in accordance with the UK Animals (Scientific Procedures) Act 1986 and associated guidelines. Male Wistar rats (initial bodyweight 125-149 g; Harlan UK Ltd) were maintained in a controlled lighting environment, four to a cage and given food and water ad libitum.

Induction of Neuropathic Pain

Neuropathic pain was induced by partial ligation of the sciatic nerve. Briefly, the rats were anaesthetised (isoflurane/$O_2$ inhalation), the left sciatic nerve exposed at mid-thigh level through a small incision and ⅓ to ½ of the nerve thickness tightly ligated within a 7.0 silk suture. The wound was closed with skin clips. Animals were allowed to recover and tested 12-15 days following surgery.

Behavioural Tests:

Mechanical Hyperalgesia

Mechanical hyperalgesia was examined in a model of neuropathic pain by measuring paw withdrawal thresholds (PWT) to increasing mechanical force applied to the dorsal surface of the rat paw using an Analgesymeter (Ugo-Basile, Milan) equipped with a wedge-shaped probe (area 1.75 mm$^2$). Cut-off was set at 250 g and the end-point was taken as withdrawal of the hind paw. Both ipsilateral and contralateral paw withdrawal readings were taken.

Cold Sensitivity

Cold sensitivity was assessed using a commercially available cold-plate (Ugo Basile, Milan). The cold-plate was set according to pre-determined calibration data using a surface temperature probe to correlate set temperature to actual surface temperature over a wide temperature range (−5° C. to 26° C.). The cold plate was allowed to stabilize for 5 minutes at the set temperature prior to testing. Paw withdrawal latencies were determined with the cold-plate set at 10° C. The animals were lightly restrained and each hind paw in turn placed onto the surface of the cold-plate. The end point was taken as the withdrawal of the paw and recorded as the withdrawal latency for the ipsilateral and the contralateral paw. A maximum cut-off of 30 seconds was used for each paw.

Testing Details and Data Handling

Withdrawal thresholds or latencies were measured on both the ipsilateral (ligated) and contralateral (non-ligated) paws. Treatment groups were randomised and blinded. Groups of 6 rats were used. Predose behavioural measurements were obtained by measuring paw withdrawals 14 days following nerve ligation; before the initiation of drug treatment. Following treatment, further readings were taken at 1, 2, 4, 6 and 24 hours after drug or vehicle administration.

Data were expressed as withdrawal threshold (g) or withdrawal latencies (s) and percentage reversals calculated according to the following formula:

$$\% \text{ reversal} = \frac{\text{ipsilateral threshold postdose} - \text{ipsilateral threshold predose}}{\text{contralateral threshold predose} - \text{ipsilateral threshold predose}} \times 100$$

General Observations

In addition to behavioural pain readings, each rat was observed throughout the study for changes in general behaviour.

Drug Administration

The compounds were made up in a vehicle containing 10% DMSO/10% Solutol HS15/80% saline. Rats were fasted overnight prior to dosing. The compounds were administered by oral gavage at 10 ml/kg bodyweight. Control animals received vehicle alone.

Compound or vehicle solutions were coded and allocated randomly to the animals (coded A-F) at predose. Data was uncoded and sorted at the end of the experiment.

Statistical Analysis

Statistical analysis was carried out on withdrawal threshold readings using ANOVA with repeated measures followed by post-hoc analysis using Tukey's HSD test. The level for statistical significance was set as $p<0.05$.

Results

Figure 2A:
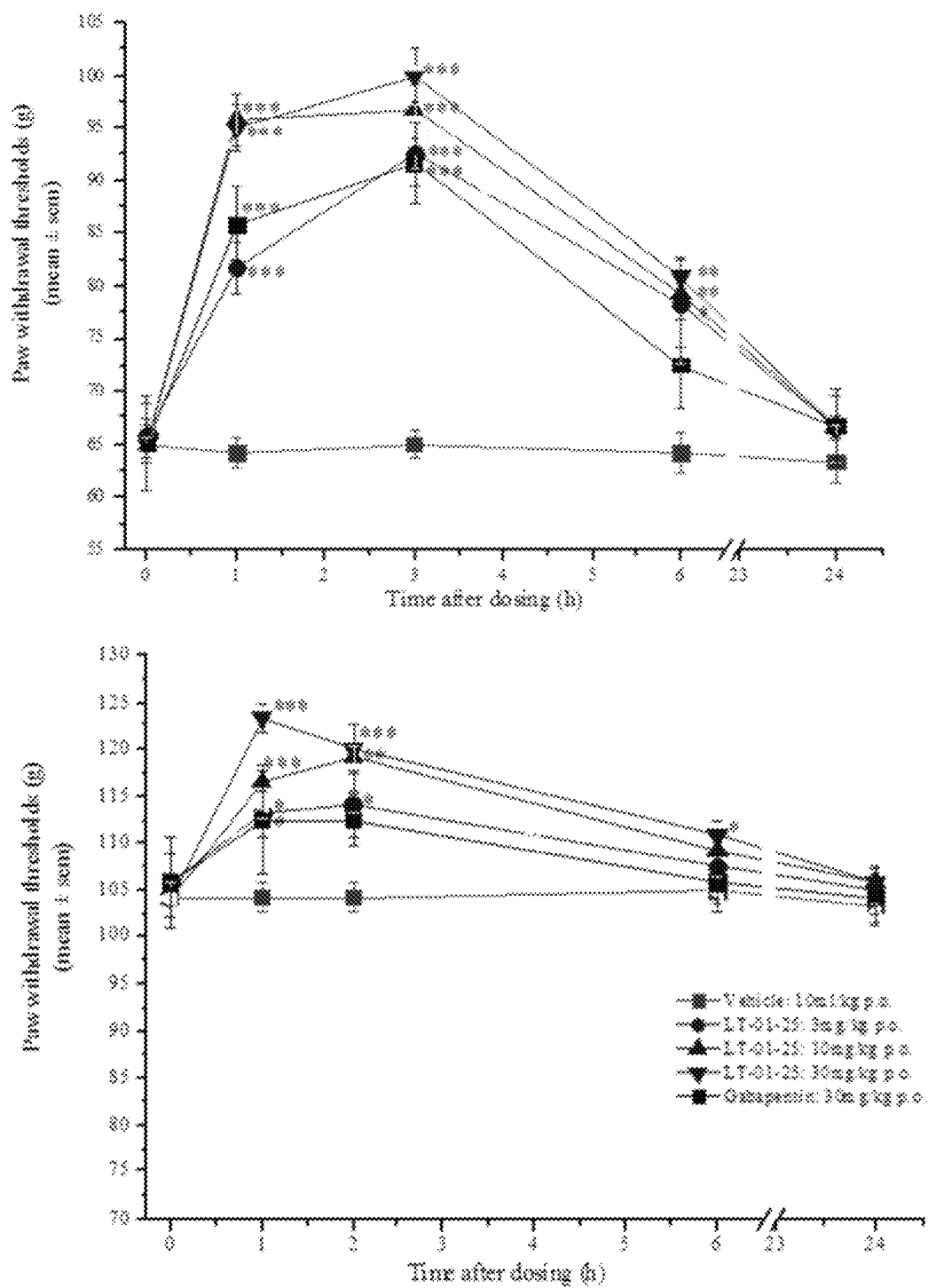
FIGS. 2A and 2B show the effect of the compound LT-01-25 on paw withdrawal thresholds to (FIG. 2A) mechanical pressure in neuropathic rats and (FIG. 2B) cold (10° C.) stimulus in neuropathic rats compared with lamotrigine (see Example 8(i))
Figure 2B:
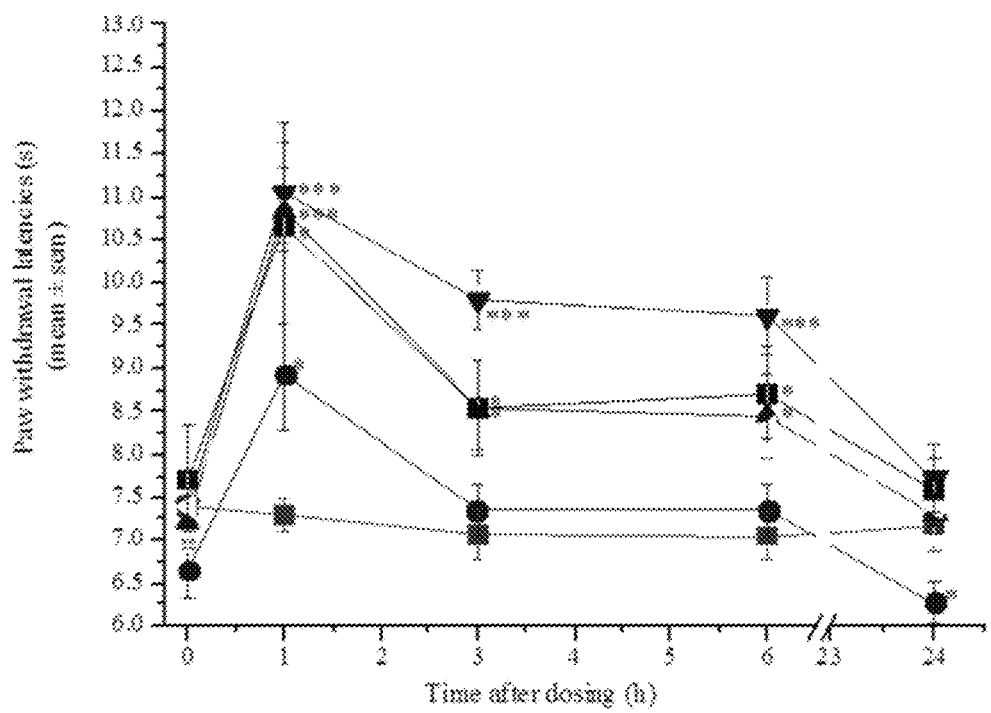
Figure 2B:
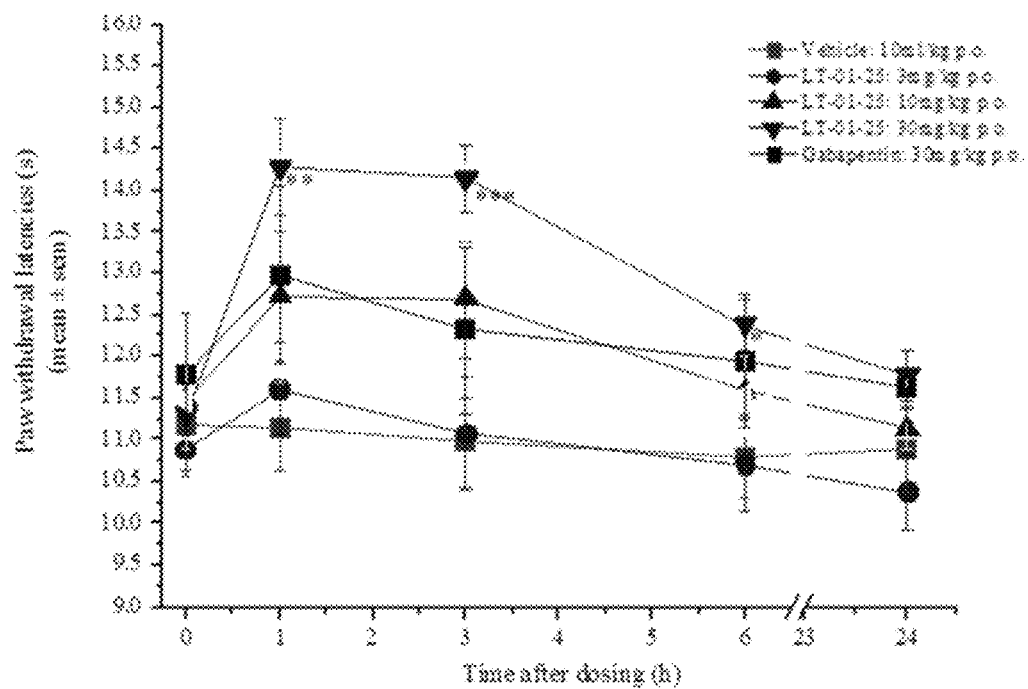

The results are shown in FIG. 2.

The LT-01-25 compound produced a marked and long-lasting reversal of both the cold (10° C. cold plate) and mechanical (paw pressure) parameters. All three doses of the LT-01-25 compound showed good and dose-related efficacy. Peak reversal of 90% with mechanical occurred at 3 h and 93% with cold occurred at 1 h. The positive control, lamotrigine, gave reversals of 65% and 72% in mechanical and cold respectively.

LT-01-25 therefore showed a significant increase in contralateral paw withdrawal thresholds to mechanical pressure. At 30 mg/kg, LT-01-25 produced increased contralateral paw withdrawal latencies to cold.

There were no apparent drug-induced behavioural side effects.

(ii) Pharmacokinetic Evaluation

Compounds—LT-01-25 (Example 1) and LT-01-89 [a comparator: (4-(hydroxy)-3,5-di-tertbutyl)(morpholino)methanone]

Dose—10 mg/kg (5 mL/kg)

Route—ORAL

Vehicles—10% DMSO/10% Solutol and SSV

Time—24 h

Procedure Number—6

Vehicles

10% DMSO/10% Solutol/80% Saline
1) Compound was weighed out into a clean vial.
2) DMSO was added into the vial; the vial was vortexed and sonicated it for 15 min.
3) Solutol HS 15 was heated at 50° C. until a liquid formed, and then was added into the vial. The vial was vortexed for 1-2 min.
4) 0.9% Saline solution was added to the vial. The vial was vortexed and then sonicated for 10 min.

Standard Suspension Vehicle (SSV)
1) A solution of SSV was made using 0.5% Sodium carboxymethylcellulose, 0.5% Benzyl alcohol, 0.4% Tween80 and 98.6% saline (0.9%)
2) Compound was weighed out into a clean vial
3) SSV solution was added into the vial; the vial was vortexed and sonicated it for 15 min.

Fasted Rats

Fasted rats were fasted overnight and given access to food immediately after dosing.

Protocol
1) Rats were manually restrained and given a 10 mg/kg oral dose of compound at 5 mL/kg.
2) At designated time points (0.25, 0.5, 1, 3, 5, 7 and 24 hours) the rats were anaesthetised using isoflurane.
3) Approximately 300 μL of blood was taken from the tail vein using a 1.5 inch needle treated with heparin and collected into 1.5 mL eppendorf tubes.
4) After sampling, pressure was applied to the puncture until bleeding ceased. The animals were returned to their cages and given free access to food and water.

5) Blood samples were stored on ice and then centrifuged at 13,000 rpm for 15 min to separate the plasma.
6) 150 μL of the plasma was treated with 300 μL of ACN:MeOH (1:1) solution containing the internal standard. The samples were then centrifuged for a further 15 min at 13,000 rpm.
7) 200 μL of the supernatant was collected and placed in LC-MS vials for analysis. All samples were stored at −80° C.

Results

Figure 3A:
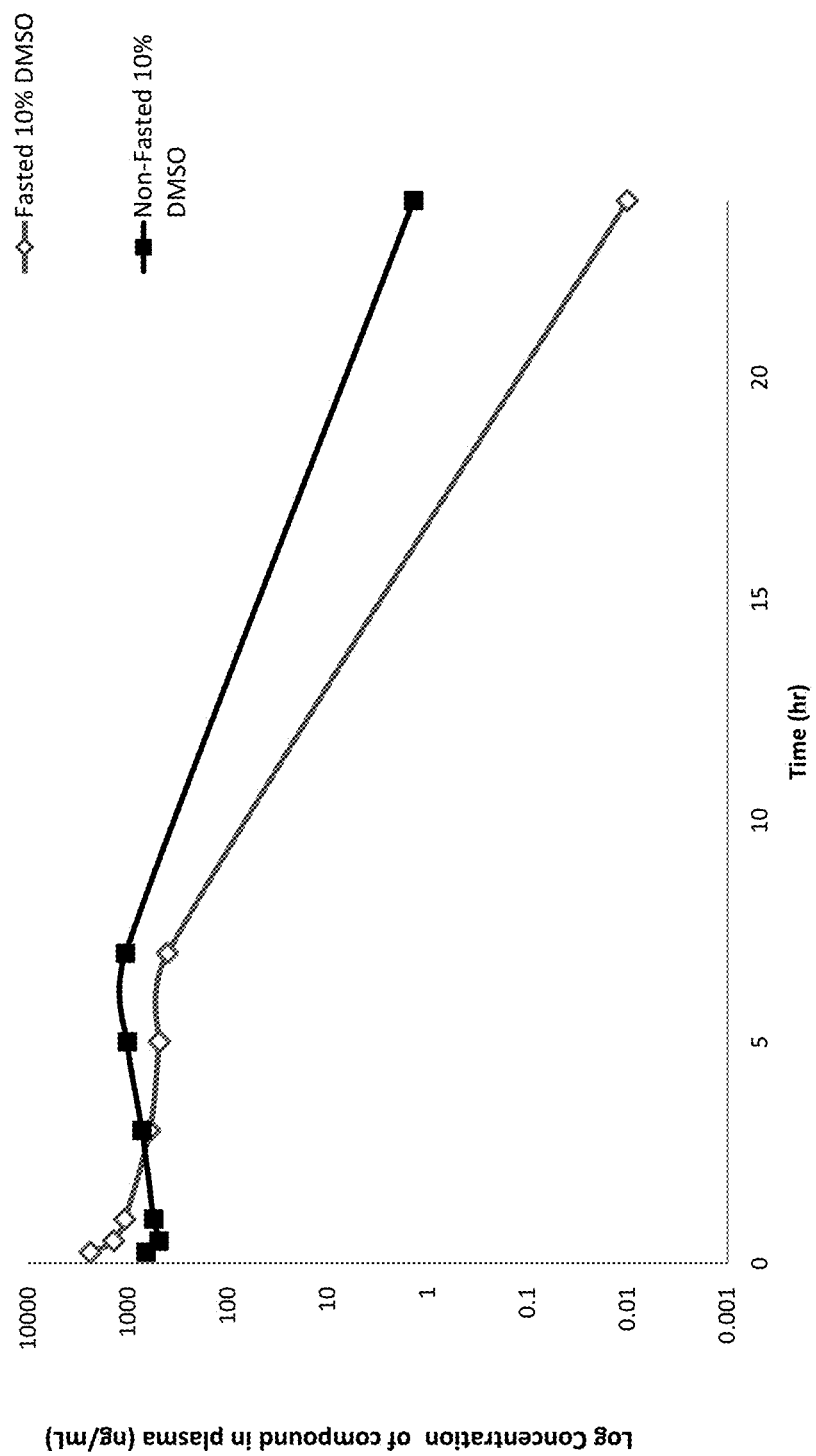
FIG. 3A shows the pharmacokinetic profile (plasma concentration (y-axis) versus time (x-axis)) for the LT-01-25 compound dosed at 10 mg/kg in 10% DMSO/10% Solutol/80% Saline in fasted and non-fasted rats.

The results for the LT-01-25 compound dosed at 10 mg/kg in 10% DMSO/10% Solutol/80% Saline in fasted and non-fasted rats are shown in FIG. 3A and in Table 1 shown below.

TABLE 1

| PK Parameters | Non-Fasted 10% DMSO | Fasted 10% DMSO |
|---|---|---|
| Half Life (hr) | 1.4 | 1.4 |
| Cmax (ng/mL) | 1710.8 | 2415.5 |
| Tmax (hr) | 4 | 0.3 |
| AUC∞ (area) (ng-hr/mL) | 20421.4 | 8532.8 |
| Vd (area)/kg (mL/kg) | 973.7 | 2300.6 |
| CL (area)/kg (mL/hr/kg) | 505.4 | 1171.9 |

Figure 3B:
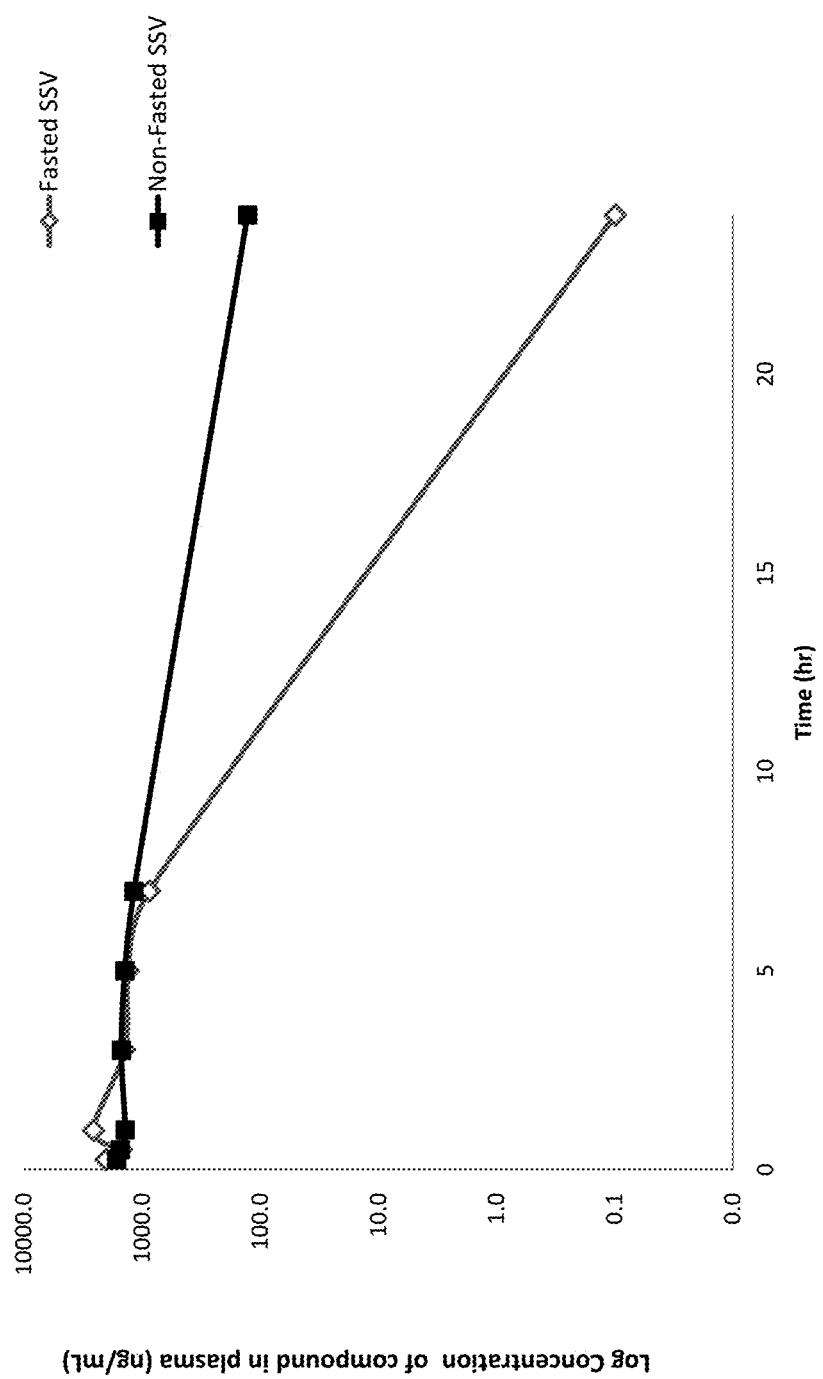
FIG. 3B shows the pharmacokinetic profile (plasma concentration (y-axis) versus time (x-axis)) for the LT-01-25 compound dosed at 10 mg/kg in SSV in fasted and non-fasted rats.

The results for the LT-01-25 compound dosed at 10 mg/kg in SSV in fasted and non-fasted rats are shown in FIG. 3B and in Table 2 shown below.

TABLE 2

| PK Parameters | Non-Fasted SSV | Fasted SSV |
|---|---|---|
| Half Life (hr) | 3.62 | 1.4 |
| Cmax (ng/mL) | 2124 | 2592.6 |
| Tmax (hr) | 0.25 | 1 |
| AUC∞ (area) (ng-hr/mL) | 19032.8 | 18130 |
| Vd (area)/kg (mL/kg) | 2710.9 | 1142.6 |
| CL (area)/kg (mL/hr/kg) | 519.7 | 551.6 |

Figure 3C:
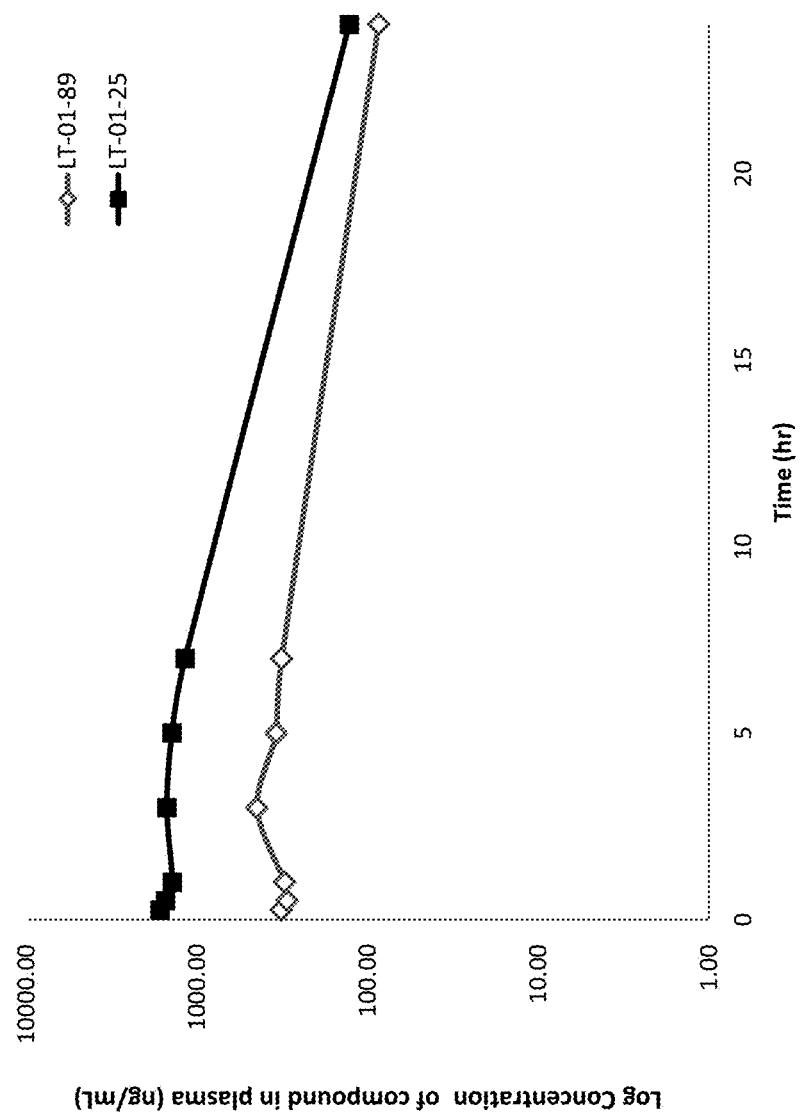
FIG. 3C shows the pharmacokinetic profile (plasma concentration (y-axis) versus time (x-axis)) for the LT-01-25 and LT-01-89 (comparator) compounds dosed at 10 mg/kg in SSV in non-fasted rats.
Figure 4A:
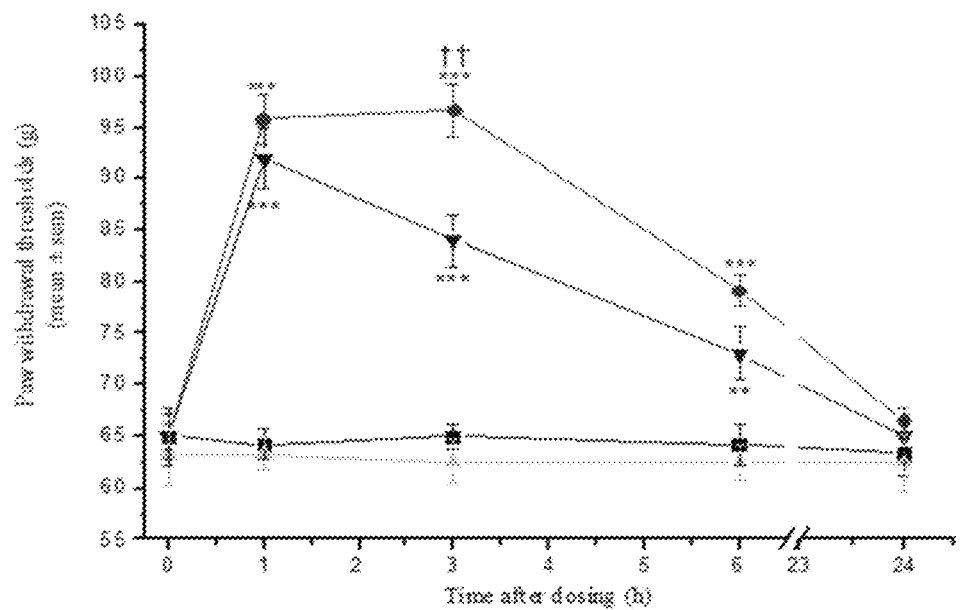
FIGS. 4A and 4B show the comparison in effect of LT-01-25 (Example 1; 10 mg/kg p.o.) and LT-01-5 89 (30 mg/kg p.o.) on (FIG. 4A) ipsilateral paw withdrawal thresholds to mechanical pressure in neuropathic rats and (FIG. 4B) ipsilateral withdrawal latencies to a cold (10° C.) stimulus in neuropathic rats. Male, SD rats. n=6/group. Vehicle: 10% DMSO/10% Solutol HS15/80% saline.
Figure 4A:
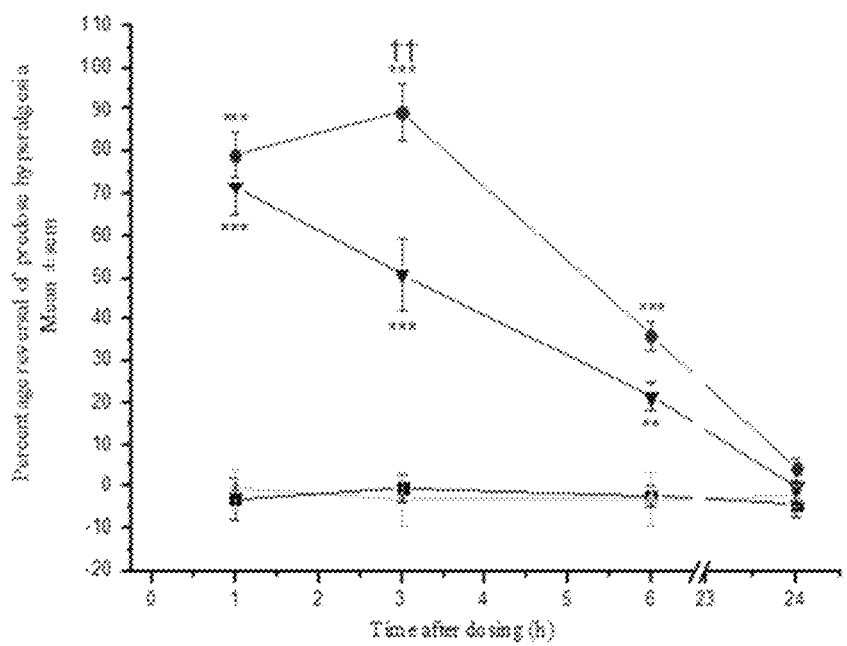
Figure 4B:
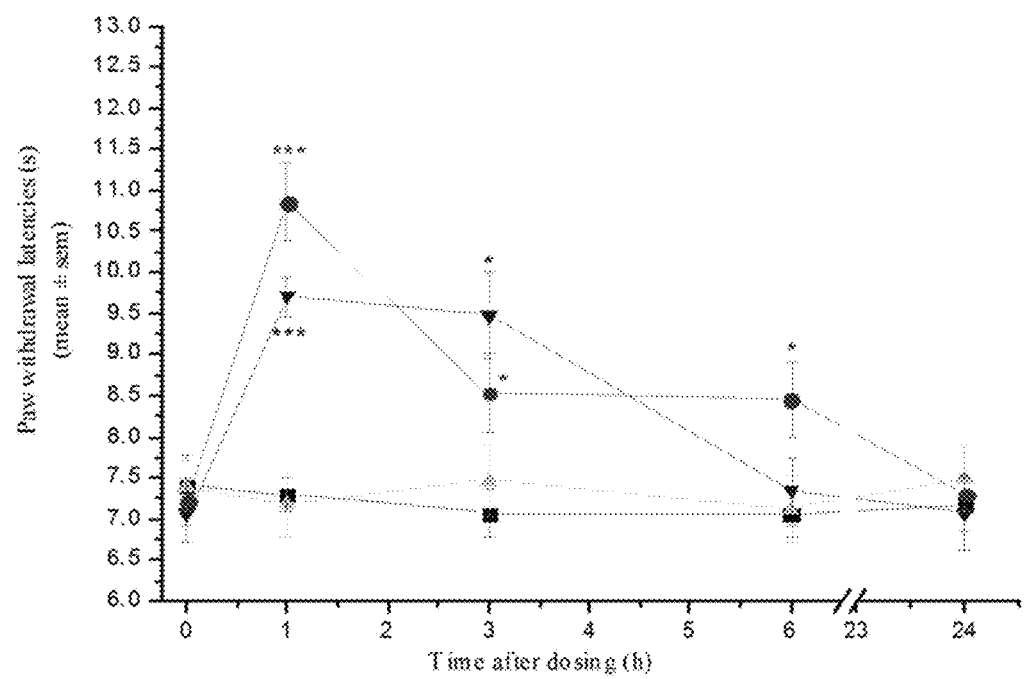
Figure 4B:
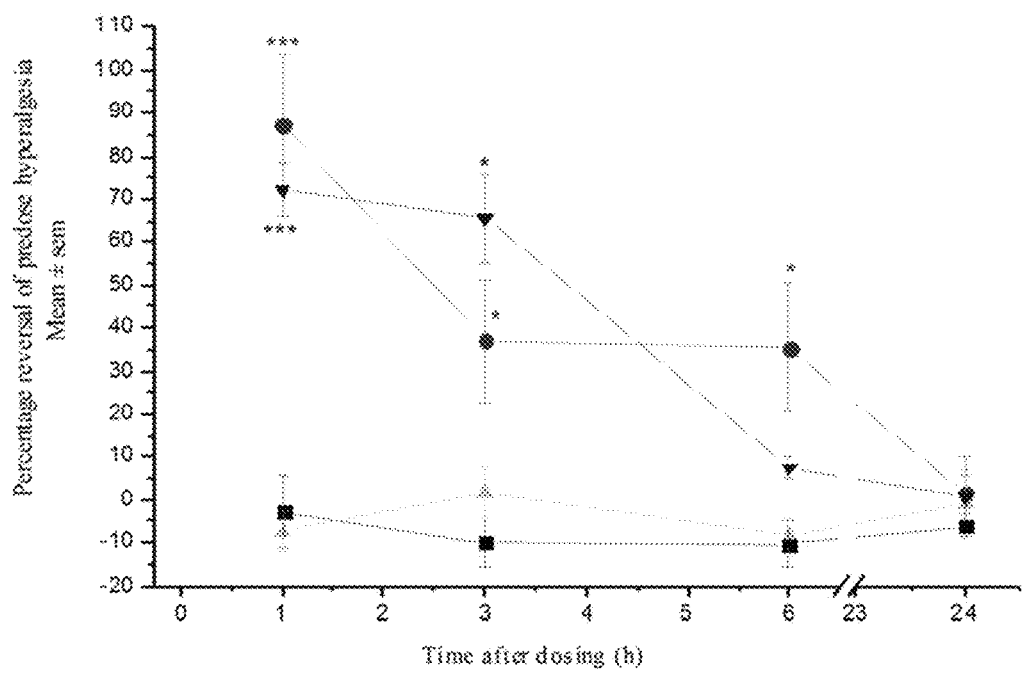

The results for the LT-01-25 and LT-01-89 (comparator) compounds dosed at 10 mg/kg in SSV in non-fasted rats are shown in FIG. 3C and in Table 3 shown below.

TABLE 3

| PK Parameters | L1-01-89 | LT-01-25 |
|---|---|---|
| Half Life (hr) | 20.4 | 3.6 |
| Cmax (ng/mL) | 471.2 | 2124.0 |
| Tmax (hr) | 1.2 | 0.3 |
| AUC∞ (area) (ng-hr/mL) | 5931.7 | 19032.8 |
| Vd (area)/kg (mL/kg) | 32729.9 | 2710.9 |
| CL (area)/kg (mL/hr/kg) | 1076.8 | 519.7 |

(iii) In Vivo Model of Neuropathic Pain: Reversal of Tactile Allodynia

A comparison of LT-01-25 (Example 1) and L1-01-89 was conducted using the following protocol:

Summary:
1) In rats a peripheral neuropathy was induced by partial ligation of the sciatic nerve in one hind limb.
2) Two weeks (12-15 days) after induction of peripheral neuropathy stable mechanical (tactile) allodynia was induced in the hind paw of the affected limb.
3) Five treatment groups of male SD rats (n=8) were used: vehicle control (drug formulation), 3 drug doses, and a positive control, lamotrigine (30 mg/kg). Animals were randomized between groups and the experiment was carried out using blinded conditions. The study was split with n=4/group in each experiment.
4) Baseline behavioural measurements were obtained prior to surgery and at intervals post-surgery. Predose behavioural measurements were obtained by measuring paw withdrawal thresholds 12-15 days following nerve ligation.
5) Compound efficacy was determined by measuring paw withdrawal thresholds at specified intervals following vehicle/compound treatment.

Methods

Animals

All animal procedures were carried out in accordance with the UK Animals (Scientific Procedures) Act 1986 and associated guidelines. Animals were maintained in a controlled lighting environment and given food and water ad libitum. Male Sprague Dawley rats (120-140 g at time of surgery) were used.

Drug Administration

Rats were fasted overnight with free access to water and fed 4 hours post-dose.

Tests compounds as well as Lamotrigine (30 mg/kg, volume: 10 ml/kg)) were prepared in the designated formulation (10% DMSO, Solutol HS 15/80% and 0.9% saline for p.o. administration) and administered via the chosen route.

Induction of Neuropathic Tactile Allodynia

Allodynia was examined in the model of neuropathic pain induced by partial ligation of the sciatic nerve as described by Seltzer et al (1990). Rats were anaesthetised (isoflurane/O2 inhalation), the left sciatic nerve was exposed at mid-thigh level through a small incision and ⅓ to ½ of the nerve thickness tightly ligated within a 7.0 silk suture. The wound was closed with skin clips. Animals were allowed to recover and compounds administered 12-15 days following surgery.

Behavioural Tests

Tactile allodynia was assessed by measuring withdrawal thresholds to calibrated von Frey hairs. As a force higher than 15 g can lift the paw as well as eliciting a response, 15 g represented the cut-off point. Animals were placed into a perspex chamber with metal grid floor giving access to the underside of their paws and allowed to acclimatise prior to the start of the experiment. Tactile allodynia was tested by touching the plantar surface of the hind paw with von Frey hairs in ascending order of force for up to 6 seconds. A positive response was noted if the paw is sharply withdrawn or there was flinching upon removal of the hair. Once a positive withdrawal response had been established, the paw was re-tested, starting with the next descending von Frey hair until no response occurred. The lowest amount of force required to elicit a response was recorded as the paw withdrawal threshold (in grams).

Data were also expressed as percentage of the maximum possible effect (% MPE) defined as:

Allodynia was measured on both the ipsilateral (ligated) and contralateral (non-ligated) paw prior to (pre-dose) and at a set time point following compound or vehicle administration (post-dose). Treatment groups were randomised and blinded. Groups of eight rats were used.

Predose behavioural measurements were obtained by measuring paw withdrawal thresholds 12-15 days following nerve ligation; before the initiation of drug treatment.

Compound/vehicle were administered at specified doses. Following treatment, further readings were taken; 1, 3, 6 and 24 hour after p.o. administration.

Statistical Analysis

Raw data were analysed using parametric statistical tests, including one-way analysis of variance (ANOVA) followed by Tukey's post hoc test repeated measures of ANOVA. P<0:05 was set as the level of statistical significance.

Reference: Seltzer Z, Dubner R, Shir Y. A novel behavioural model of neuropathic pain disorders produced in rats by partial sciatic nerve injury. Pain 1990; 43:205±218.

Results

The results are shown in FIG. 4 and Table 4 below:

TABLE 4 comparison of LT-01-25 and L1-01-89

|  | LT-01-25 (10 mg/kg) | LT-01-89 (30 mg/kg) |
|---|---|---|
| Mechanical pressure | 1 hr - - - 80% | 1 hr - - - 70% |
| Percentage reversal of predose hyperalgesia | 3 hr - - - 90% | 3 hr - - - 50% |
|  | 6 hr - - - 40% | 6 hr - - - 20% |
| Cold (10° C.) Stimulus | 1 hr - - - 85% | 1 hr - - - 70% |
| Percentage reversal of predose Hyperalgesia after 1 hr | 3 hr - - - 35% | 3 hr - - - 65% |
|  | 6 hr - - - 35% | 6 hr - - - 10% |

(iv) Cerebrospinal Fluid (CSF) and Plasma Levels

| Test system | SD rat, 243-272 g, male, N = 9, purchased from SLAC Laboratory Animal Co. LTD |
|---|---|
| Food status | Fasted overnight, free access to water and fed 4 hr post dose. |
| Administration | PO: 3 mg/kg (10 mL/kg) via oral gavage (N = 9) |
| Blood collection | The animal was restrained manually at the designated time points, approximately 150 μL of blood sample was collected via cardioac puncture into EDTA-2K tubes. The blood samples were maintained in wet ice first and centrifuged to obtain plasma (2000 g, 4° C., 10 min) within 30 minutes post sampling. |
| CSF collection | 1. The animal was euthanized under pure $CO_2$.<br>2. The CSF was collected by direct puncture of butterfly needle into the cisterna magna, using the occipital bone and the wings of the atlas as landmarks.<br>3. A piece of white paper was used as a background to monitor color change in the sample just above the needle during collection.<br>4. Upon observation of color change, the PE tubing was quickly clamped off above the color change and cut just above the clamped site. The clear sample is drawn into the syringe. |
| Sample storage and disposition | Plasma samples will be stored in dry ice temporarily and transferred into-80° C. freezer for long term preservation. The backup samples will be discarded after 3 weeks unless specified. The unused dosing solutions will be stored at 4° C. fridge and discarded within 1 week after completion of the study. |

Results

The results are shown in Table 5 below.

TABLE 5

CSF data for LT-01-25 and L1-01-89 (comparator)

|  | LT-01-25 | LT-01-89 |
|---|---|---|
| CSF levels (p.o. dose 3 mg/kg after 2 hr) | 95 ng/mL (900 × $EC_{50}$) | 27 ng/mL (180 × $EC_{50}$) |

(v) Microsomal Stability Data

Rat and human microsomal stability data was obtained using well established protocols known to those skilled in the art.

The human microsomal stability protocol is detailed below.

Human Microsomal Data

Incubation Methods

The metabolic stability assay was performed by incubating each test compound (1 μM) with human liver microsomes in duplicate at 37° C. and 0.4 mg/mL protein concentration. The metabolic reaction was initiated by the addition of a NADPH-regenerating system (i.e. NADPH is the cofactor required for CYP450-mediated metabolism) and quenched at various time points over the 60 minute incubation period by the addition of acetonitrile. Control samples (containing no NADPH) were included (and quenched at 2, 30 and 60 minutes) to monitor for potential degradation in the absence of cofactor. Samples were analysed by UPLC-MS (Waters/Micromass Xevo G2 QTOF) under positive electrospray ionisation and MS spectral data acquired in a mass range of 80 to 1200 Daltons.

Calculations

Test compound concentration versus time data were fitted to an exponential decay function to determine the first-order rate constant for substrate depletion. In cases where clear deviation from first-order kinetics was evident, only the initial linear portion of the profile was utilised to determine the degradation rate constant (k). Each substrate depletion rate constant was then used to calculate: [1] a degradation half-life, [2] an in vitro intrinsic clearance value (CLint, in vitro); [3] a predicted in vivo hepatic intrinsic clearance value (CLint); [4] a predicted in vivo blood clearance value (CLblood); and [5] a predicted in vivo hepatic extraction ratio (EH).

[1] $$t_{1/2} = \frac{\ln(2)}{k}$$

[2] $$CL_{int, in\ vitro} = \frac{k}{\text{microsomal protein content (0.4 mg protein/mL)}}$$

[3]* $$CL_{int} = CL_{int, \text{in vitro}} \times \frac{\text{liver mass (g)}}{\text{body weight (kg)}} \times \frac{\text{mg microsomal protein}}{\text{g liver mass}}$$

[4]* $$CL_{blood} = \frac{Q \times CL_{int}}{Q + CL_{int}}$$

[5]* $$E_H = \frac{CL_{blood}}{Q} = \frac{CL_{int}}{Q + CL_{int}}$$

*The following scaling parameters[a] were assumed in the above calculations:

| Species | Liver Mass (g liver/kg body weight) | Microsomal protein (mg/g liver mass) | Hepatic blood flow (Q) (mL/min/kg body weight) |
|---|---|---|---|
| Human | 25.7 | 32 | 20.7 |

[a]Ring et al. (2011) *Journal of Pharmaceutical Sciences*, 100:4090-4110.

NOTE:
Calculations of intrinsic clearance are based on the "in vitro $T_{1/2}$ method" (Obach, 1999, *Drug Metab. Dispos.* 27: 1350-1359), which assumes:
1) The substrate concentration employed is well below the apparent $K_M$ for substrate turnover; and,
2) There is no significant product inhibition, nor is there any mechanism-based inactivation of enzyme.

The use of hepatic microsomes in the prediction of the in vivo hepatic extraction ratio has two further inherent assumptions (Obach, 1999) which:
1) NADPH-dependent oxidative metabolism predominates over other metabolic routes (i.e. direct conjugative metabolism, reduction, hydrolysis, etc.); and,
2) Rates of metabolism and enzyme activities in vitro are truly reflective of those that exist in vivo.

Data should be considered within these terms of reference.

The limit of sensitivity of this assay corresponds to 15% loss of compound over the assay duration. For compounds showing <15% loss over 60 minutes (i.e. degradation half-life >247 min), metabolic stability parameters based on 0.4 mg/mL microsomal protein concentration are reported as below:

| Species | In vitro $CL_{int}$ (μL/min/mg protein) | Microsome-Predicted $E_H$ |
|---|---|---|
| Human | <7 | <0.22 |
| Rat | <7 | <0.15 |
| Mouse | <7 | <0.13 |

Results

The results for the rat and human microsomal studies are shown in Table 6 below:

TABLE 6

Rat and human microsomal data for LT-01-25 and L1-01-89 (comparator)

| Microsome used | LT-01-25 | L1-01-89 |
|---|---|---|
| Rat microsomes (1 μM) ($t_{1/2}$), CI | 741 min, 3.35 mL/min/kg 1155 min ($t_{1/2}$)* 1.07 mL/min/kg (CI)* | 121 min 20.38 mL/min/kg 165 min ($t_{1/2}$)* 5.26 mL/min/kg (CI)* |
| human microsomes (1 μM) ($t_{1/2}$), CI | 495 min ($t_{1/2}$)* 2.7 mL/min/kg (CI)* | 138.6 min ($t_{1/2}$)* 6.2 mL/min/kg (CI)* |

Example 9—Biological Evaluation of LT-01-26 (Example 6)

The effect of LT-01-26 on percentage reversal to cold (10° C.) stimulus was investigated using the protocol described in Example 8, section (iii) above. In all cases fasted, male, Wistar rats were used (n=6/group). The vehicle was 10% DMSO/10% Solutol HS15/80% saline. 10 ml/kg p.o. was administered. The results were subject to one-way ANOVA, comparison with time-matched vehicle group using Tukey's HSD test * $p<0.05$,  $p<0.01$, * $p<0.001$.

Results

Figure 5:
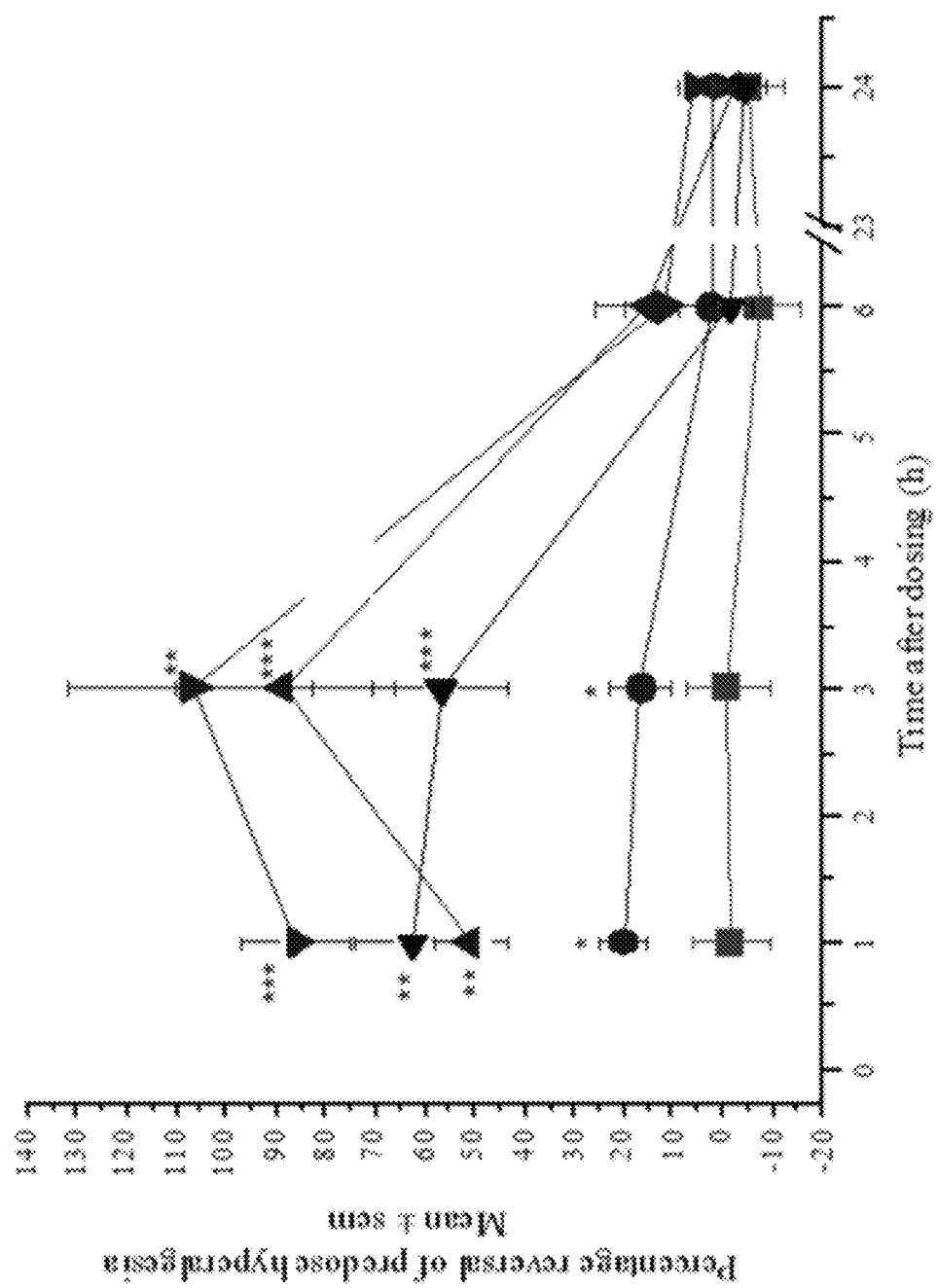
FIG. 5 shows the effect of LT-01-26 (example 6) on percentage reversal to cold (10° C.) stimulus. In all cases fasted, male, Wistar rats were used (n=6/group). Vehicle: 10% DMSO/10% Solutol HS15/80% saline. 10 ml/kg p.o. One-way ANOVA, comparison with time-matched vehicle group using Tukey's HSD test * p<0.05,  p<0.01, * p<0.001.

The results are shown in FIG. 5.

Example 10—Streptozocin-Induced Diabetic Neuropathic Pain Model

The efficacy of LT-01-25 on mechanical allodynia in Streptozocin (STZ) induced neuropathic rats was measured using the methodology described below. Comparative data for the efficacy of Gabapentin (Gbp) was also generated.

Method

Mechanical allodynia was measured using hindpaw withdrawal threshold (PWT) using von Frey hair test. In all cases Wistar rats (~200 g, SLAC) were used. Streptozocin, obtained from Sigma, was injected intraperitoneally (IP injection) at time zero (0 days). An effect amount of 60 mg/kg of Streptozocin was injected. PWT and blood glucose tests were then measured after 7 days (blank (BL)) before the vehicle or compound was administered and further PWT measurements were taken at either 1, 3, 4 and 6 hours, 1, 3 and 6 hours or 3, 6, 9 and 12 hours after vehicle or compound administration.

Compounds Used:

Vehicle II (DSS): 10% DMSO+1% Solutol+80% Saline, p.o. 10 mg/kg

Gabapentin: 30, 60 mg/kg in DSS, p.o. 10 ml/kg

LT-01-25: 3, 10, 30 and 100 mg/kg in DSS, p.o. 10 ml/kg

Results

Figure 6A:
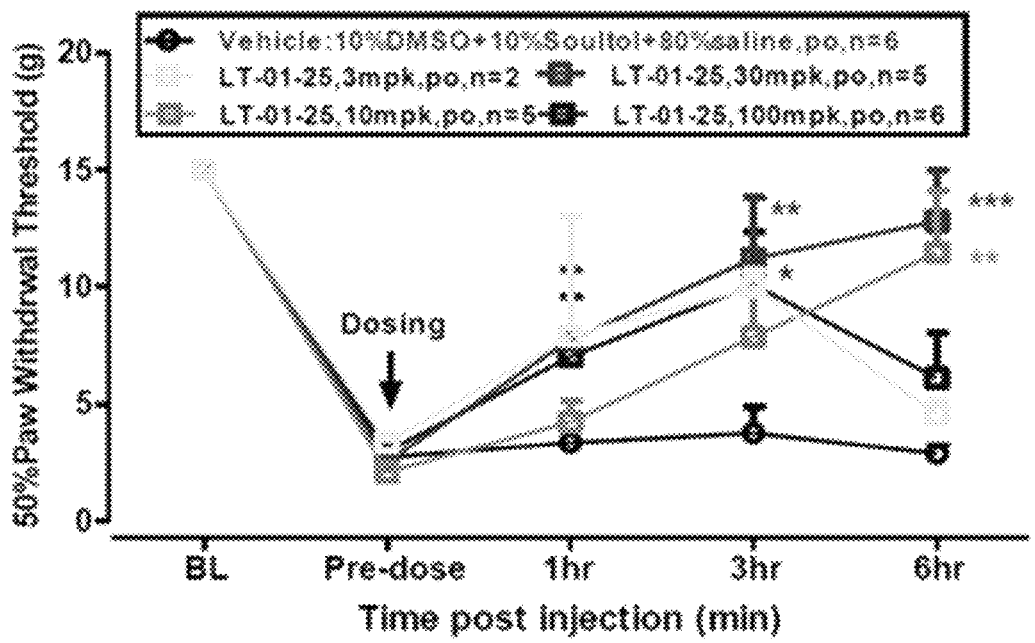
FIGS. 6A and 6B show the efficacy of (FIG. 6A) LT-01-25 and (FIG. 6B) Gabapentin-on mechanical allodynia in Streptozocin (STZ) induced neuropathic rats. In all cases Wistar rats were used (n=2-6). Vehicle: 10% DMSO+1% Solutol+80% Saline, p.o. 10 mg/kg. The following administrative doses were used; Gabapentin: 30, 60 mg/kg in DSS, p.o. 10 ml/kg; and LT-01-25: 3, 10, 30 and 100 mg/kg in DSS, p.o. 10 ml/kg.
Figure 6B:
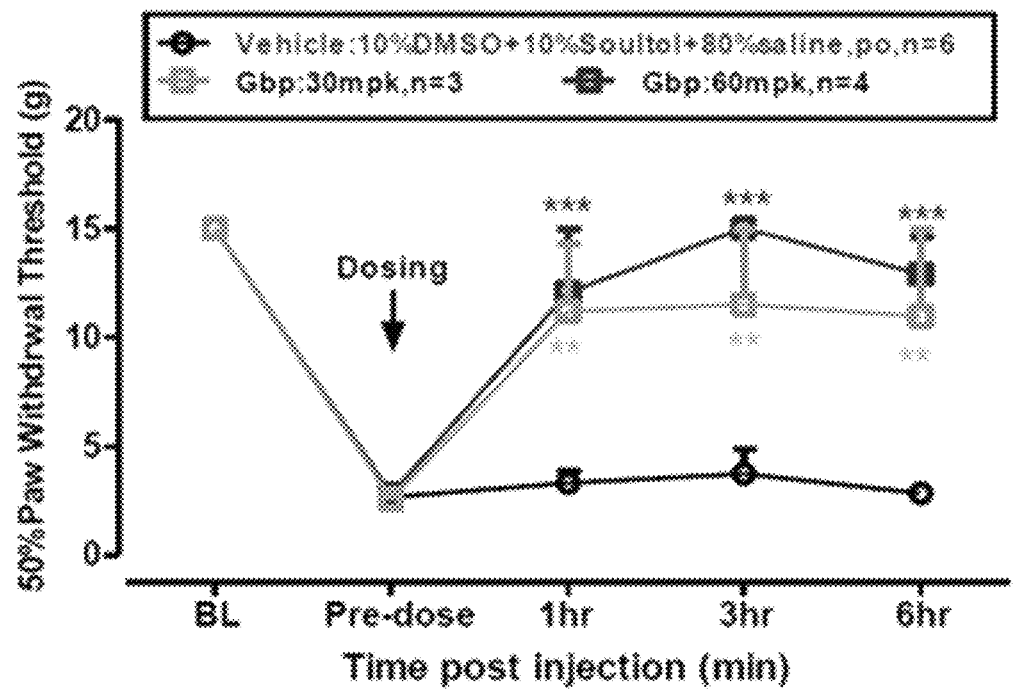

The results are shown in FIGS. 6(a) and 6(b).

The invention claimed is:
1. A compound of formula (I) shown below:

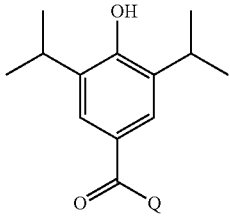 (I)

wherein:
Q is:

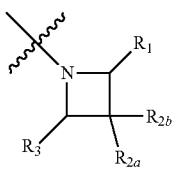

wherein:
∿∿∿ indicates the point of attachment to the C(=O) moiety of the compound of formula I; and
$R_1$, $R_{2a}$, $R_{2b}$ and $R_3$ are each independently selected from hydrogen, halo, methyl, hydroxymethyl, $CF_3$ and $OCF_3$; or $R_{2a}$ and $R_{2b}$ are linked such that together they form a 4, 5 or 6- membered carbocyclic or heterocyclic ring;
or a pharmaceutically acceptable salt thereof.

2. A compound according to claim 1, wherein $R_1$, $R_{2a}$, $R_{2b}$ and $R_3$ are each independently selected from hydrogen, fluoro or methyl; or $R_{2a}$ and $R_{2b}$ are linked such that together they form a 4 or 5 membered carbocyclic or heterocyclic ring.

3. A compound according to claim 1, wherein $R_1$, $R_{2a}$, $R_{2b}$ and $R_3$ are all hydrogen; or $R_{2a}$ and $R_{2b}$ are linked such that together they form a 4 or 5 membered heterocyclic ring.

4. A compound according to claim 1, wherein one or two of $R_1$, $R_{2a}$, $R_{2b}$ and $R_3$ is a substituent other than hydrogen.

5. A compound according to claim 1, wherein $R_1$ and $R_3$ are hydrogen and one of $R_{2a}$ and $R_{2b}$ is fluoro.

6. A compound according to claim 1, which is selected from any one of the following:
(3-fluoroazetidin-1-yl)(4-hydroxy-3,5-diisopropylphenyl)methanone; and
(4-Hydroxy-3,5-diisopropylphenyl)(2-oxa-6-azaspiro[3.3]heptan-6-yl)methanone;
or a pharmaceutically acceptable salt or solvate thereof.

7. A pharmaceutical composition comprising a compound according to claim 1, or a pharmaceutically acceptable salt thereof, in admixture with a pharmaceutically acceptable diluent or carrier.

8. A method of treating chronic pain or inducing anaesthesia in a patient in need of such treatment, said method comprising administering to said patient a therapeutically effective amount of a compound according to claim 1.

9. A method of synthesising a compound of claim 1, or a pharmaceutically acceptable salt or solvate thereof, the method comprising:
a) reacting a compound of formula A

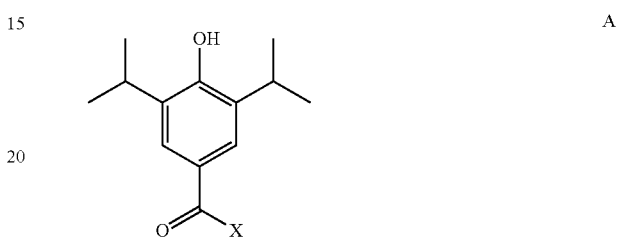

wherein X is a reactive group, for example chloro; and the hydroxyl group is optionally protected;
with a compound of formula B:

H-Q wherein the H atom is attached to a nitrogen atom of the Q group.

10. A pharmaceutical composition comprising a compound according to claim 6, or a pharmaceutically acceptable salt thereof, in admixture with a pharmaceutically acceptable diluent or carrier.

11. A method of treating chronic pain or inducing anaesthesia in a patient in need of such treatment, said method comprising administering to said patient a therapeutically effective amount of a compound according to claim 6.

12. A compound according to claim 1, wherein $R_1$, $R_{2a}$, $R_{2b}$ and $R_3$ are each independently selected from hydrogen or fluoro.

13. A compound according to claim 1, wherein $R_{2a}$ and $R_{2b}$ are linked such that together they form a 4 or 5 membered carbocyclic or heterocyclic ring.

14. A compound according to claim 1 which is (3-fluoroazetidin-1-yl)(4-hydroxy-3,5-diisopropylphenyl)methanone, or a pharmaceutically acceptable salt or solvate thereof.

15. A compound according to claim 1 which is (4-hydroxy-3,5-diisopropylphenyl)(2-oxa-6-azaspiro[3.3]heptan-6-yl)methanone, or a pharmaceutically acceptable salt or solvate thereof.

* * * * *